US008511226B2

(12) United States Patent
Knorr et al.

(10) Patent No.: US 8,511,226 B2
(45) Date of Patent: Aug. 20, 2013

(54) PEPPER DE-STEMMING METHODS AND APPARATUS

(76) Inventors: Robert J. Knorr, Maricopa, AZ (US); John Victor, Cochise, AZ (US)

( * ) Notice: Subject to any disclaimer, the term of this patent is extended or adjusted under 35 U.S.C. 154(b) by 0 days.

(21) Appl. No.: 13/278,172

(22) Filed: Oct. 20, 2011

(65) Prior Publication Data

US 2012/0294991 A1    Nov. 22, 2012

Related U.S. Application Data

(63) Continuation-in-part of application No. 12/104,334, filed on Apr. 16, 2008.

(60) Provisional application No. 60/912,405, filed on Apr. 17, 2007, provisional application No. 60/947,281, filed on Jun. 29, 2007, provisional application No. 61/016,071, filed on Dec. 21, 2007.

(51) Int. Cl.
*A23N 15/02* (2006.01)
*A23N 15/04* (2006.01)
*A23L 1/212* (2006.01)
*G01N 9/24* (2006.01)

(52) U.S. Cl.
CPC ............. *A23N 15/02* (2013.01); *A23N 15/04* (2013.01); *A23L 1/212* (2013.01); *G01N 9/24* (2013.01)
USPC ............ 99/642; 99/489; 99/491; 99/635; 99/637; 99/640; 99/643; 426/231; 426/484; 460/134

(58) Field of Classification Search
CPC ........ A23N 15/02; A23N 15/04; A23L 1/212; G01N 9/24
USPC .......... 99/635, 636, 637, 640, 642, 643, 99/489, 491; 426/234, 484; 460/134
See application file for complete search history.

(56) References Cited

U.S. PATENT DOCUMENTS

| | | | | |
|---|---|---|---|---|
| 3,080,904 A | * | 3/1963 | Carmichael | 99/643 |
| 3,349,905 A | * | 10/1967 | Crawford | 209/586 |
| 3,621,900 A | * | 11/1971 | Rood | 99/636 |

(Continued)

FOREIGN PATENT DOCUMENTS

WO    WO03103419 A1    12/2003

OTHER PUBLICATIONS

Attachment 1 of 7 Chilie Task Force Engineering etc From Peacock Myers.
Attachment 2 of 7 Mechanization Projects Update Feb. 6, 2006.

(Continued)

*Primary Examiner* — Gene Kim
*Assistant Examiner* — Alexander Niconovich
(74) *Attorney, Agent, or Firm* — Paul B. Heynssens Attorney At Law, PLC

(57) ABSTRACT

A way of dealing with challenges to the pepper processing industry and pepper growers is to mechanize pepper processing, including the de-stemming of whole peppers. The present example provides a method for mechanically de-stemming whole peppers. The method provides for the recognition of a pepper's shoulder and or interior regions and stem in order to generate a control signal to initiate a process to de-stem the pepper. In particular, several implementations of the method are provided that may include a mechanical system, a laser system, a machine vision system, a combination of a machine vision system and the laser system, and other equivalent implementations. Additionally disclosed, are methods of processing whole peppers utilizing automated de-stemming.

17 Claims, 35 Drawing Sheets

(56) References Cited

U.S. PATENT DOCUMENTS

| | | | |
|---|---|---|---|
| 3,732,764 A * | 5/1973 | Gerber | 83/34 |
| 3,820,450 A * | 6/1974 | Rasmussen et al. | 99/643 |
| 3,845,703 A * | 11/1974 | Gillespie | 99/491 |
| 3,845,705 A * | 11/1974 | Chapman | 99/643 |
| 3,878,745 A * | 4/1975 | Handziak et al. | 83/61 |
| 4,054,970 A * | 10/1977 | Metzger et al. | 452/4 |
| 4,138,940 A * | 2/1979 | Fujii | 99/636 |
| 4,328,725 A * | 5/1982 | Gschwend | 83/27 |
| 4,337,693 A * | 7/1982 | Dandrea | 99/491 |
| 4,361,084 A * | 11/1982 | Raatz | 99/516 |
| 4,367,675 A * | 1/1983 | Boots | 99/546 |
| 4,372,184 A * | 2/1983 | Fisher et al. | 83/98 |
| 4,416,195 A * | 11/1983 | Miller | 99/544 |
| 4,576,071 A * | 3/1986 | Rayment | 83/76.8 |
| 4,596,182 A * | 6/1986 | del Ser Gonzalez | 99/491 |
| 5,060,547 A * | 10/1991 | Moriya et al. | 83/210 |
| 5,335,571 A * | 8/1994 | Pike | 83/13 |
| 5,390,590 A * | 2/1995 | Mendenhall | 99/537 |
| 5,477,762 A * | 12/1995 | Meulnart | 83/364 |
| 5,495,797 A * | 3/1996 | Meulnart | 99/637 |
| 5,544,558 A * | 8/1996 | Hughes | 83/75.5 |
| 5,550,927 A * | 8/1996 | Zittel et al. | 382/110 |
| 5,590,591 A * | 1/1997 | Kim | 99/544 |
| 5,727,132 A * | 3/1998 | Arimatsu et al. | 700/259 |
| 5,862,728 A * | 1/1999 | Giamello | 83/13 |
| 5,916,354 A * | 6/1999 | Dragt | 99/536 |
| 5,957,304 A * | 9/1999 | Dawson | 209/552 |
| 5,969,339 A * | 10/1999 | McMurray et al. | 250/223 R |
| 6,036,989 A * | 3/2000 | Ellis | 426/484 |
| 6,070,509 A * | 6/2000 | Lonn et al. | 83/34 |
| 6,563,904 B2 * | 5/2003 | Wijts et al. | 378/58 |
| 6,567,162 B2 * | 5/2003 | Koren et al. | 356/237.2 |
| 6,648,730 B1 * | 11/2003 | Chokshi et al. | 451/6 |
| 6,684,748 B2 * | 2/2004 | Mendenhall | 83/369 |
| 6,873,880 B2 * | 3/2005 | Hooke et al. | 700/159 |
| 6,988,622 B1 * | 1/2006 | Victor | 209/162 |
| 7,096,777 B1 * | 8/2006 | Healy | 99/542 |
| 7,409,905 B2 * | 8/2008 | Huddle | 99/636 |
| 7,559,275 B1 * | 7/2009 | Patil et al. | 99/537 |
| 8,272,322 B2 * | 9/2012 | Benedetti | 99/638 |
| 2002/0166431 A1 * | 11/2002 | Benjamin et al. | 83/423 |
| 2008/0289515 A1 * | 11/2008 | Knorr et al. | 99/640 |
| 2011/0293797 A1 * | 12/2011 | Pryor et al. | 426/231 |

OTHER PUBLICATIONS

Attachment 3 of 7 Destemmer Update of Jun. 1, 2006.
Attachment 4 of 7 Destemmer Update of Dec. 14, 2006.
Attachment 5 of 7 Destemmer Update of Feb. 6, 2007.
Attachment 6 of 7 Destemmer Update of Jun. 19, 2007.
Attachment 7 of 7 Destemmer Update of Oct. 5, 2007.
Knorr Letter from Peacock Myers of Aug. 7, 2009.

* cited by examiner

FIG. 27

PEPPER DE-STEMMING METHODS AND APPARATUS

CROSS-REFERENCE TO RELATED APPLICATIONS

This is a continuation-in-part of application Ser. No. 12/104,334, filed Apr. 16, 2008 which claims priority to provisional patent application No. 60/912,405 filed Apr. 17, 2007; provisional application No. 60/947,281 filed on Jun. 29, 2007; and provisional application No. 61/016,071 filed on Dec. 21, 2007, the disclosures of which is incorporated herein by reference. This application is related to issued U.S. Patent entitled "PEPPER BOAT MAKER AND PROCESS FOR MAKING SAME", U.S. Pat. No. 7,887,865, issued Feb. 15, 2011.

TECHNICAL FIELD

This description relates generally to food harvesting and processing and more specifically to the harvesting and processing of fruits and vegetables having features that may include a recognizable shoulder, a stem and a pulpy interior, such as whole peppers and the like.

BACKGROUND

Harvesting and processing of fruits and vegetables such as whole peppers is typically labor intensive. For example, when whole peppers are picked, they are usually hand graded in the field. Likewise, de-stemming is a labor intensive process to remove the stem and the calyx of the pepper from the pepper pod. De-stemming may be done in the field at harvest, or may be done by hand during processing of the whole peppers, typically before the whole peppers are processed for products, such as salsa, or are processed further, such as being canned.

A trend in the agriculture industry is the increase in labor costs and the continuing effort to find low cost labor, typically migrant or seasonal laborers. However, the availability of this low cost labor source has recently diminished. This decrease in the availability of cost effective local labor can create challenges to a grower's ability to harvest and process whole peppers. In addition, processing may be outsourced to foreign countries where labor may be available at low cost, but adding transportation costs to the total cost of processing. It might be advantageous to grow and economically process fruits and vegetables such as peppers locally, so that freshness is Improved and transportation costs minimized.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

A way of dealing with challenges to the pepper processing industry and pepper growers is to mechanize pepper processing, including the de-stemming of whole peppers. The present example provides a method of for mechanization of the de-stemming of whole peppers. This process applies equivalently to other types of fruits and vegetables. The methods described provide for the recognition of a pepper's shoulder in order to generate a control signal to initiate a process to de-stem the pepper. In particular, several implementations of the method are provided that may include a mechanical system, a laser system, a machine vision system, a combination of a machine vision system and the laser system, and other equivalent implementations. De-stemming may also be accomplished by examining interior characteristics of a pepper, such as the density of the stem and placenta in order to determine where to de-stem the pepper. Additionally disclosed, are methods of processing whole peppers utilizing mechanized de-stemming.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

I. De-Stemming Based on Evaluation of the Exterior

I. A. De-Stemmers

Figure 3:
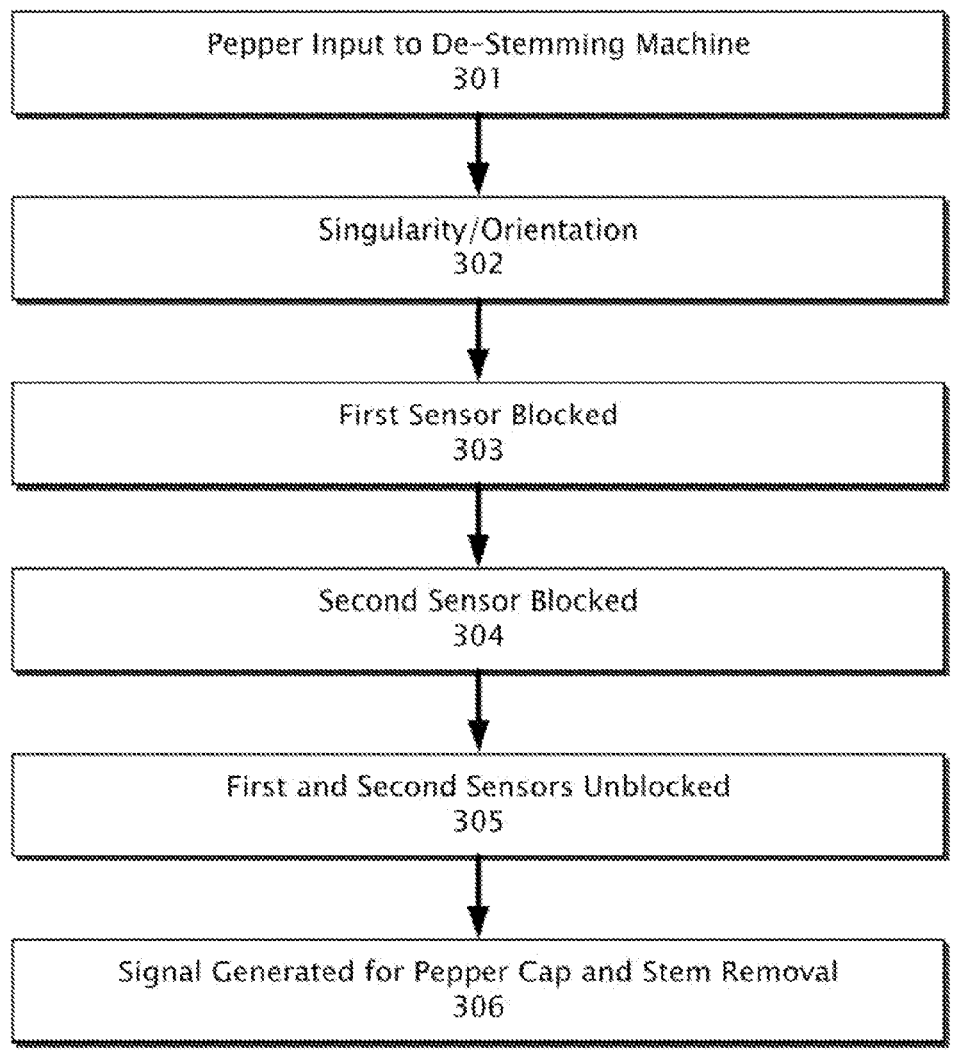

FIG. 3 is a flow chart of a method of de-stemming a pepper utilizing mechanical or laser, shoulder recognition based on exterior examination.

Figure 4:
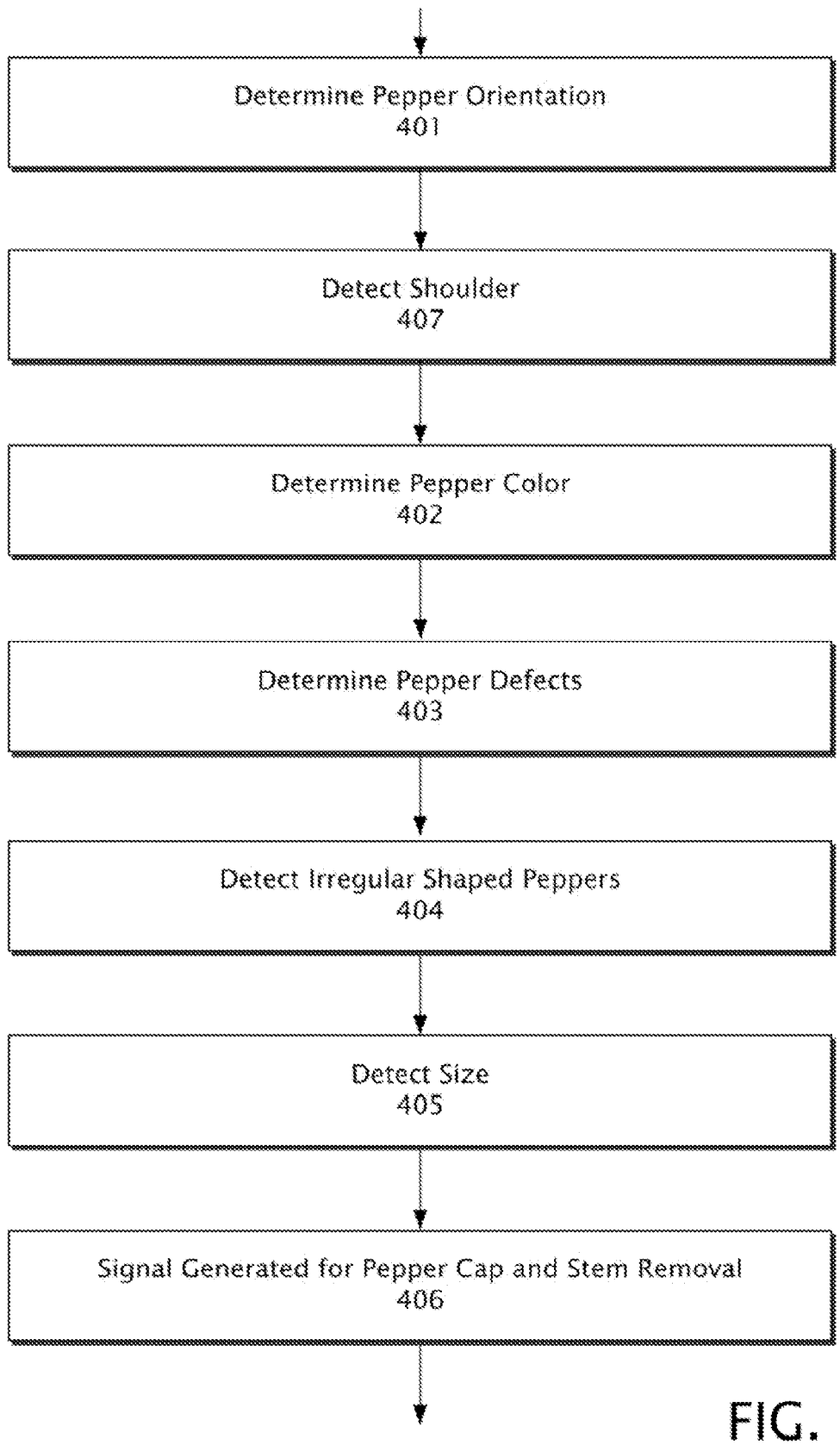

FIG. 4 is a flow chart of a method of de-stemming a pepper utilizing machine vision or a combination of machine vision and laser shoulder recognition that examines an image made of the pepper.

Figure 5:
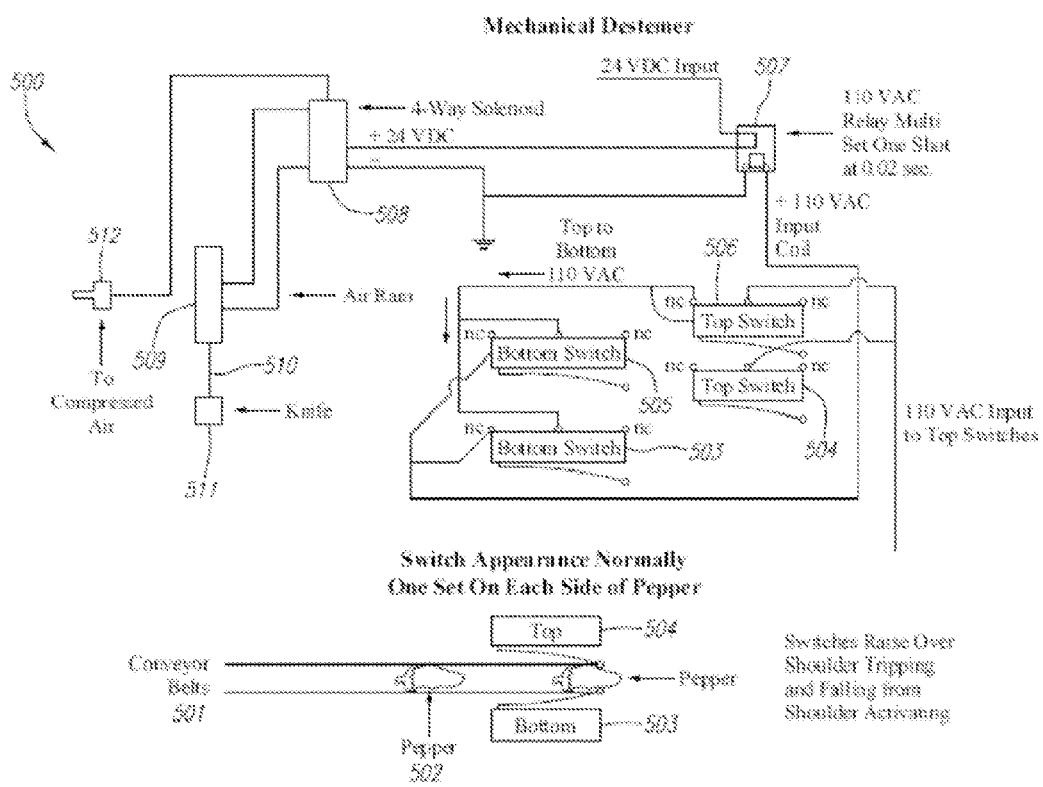

FIG. 5 is a schematic showing a first example of pepper de-stemmer utilizing mechanical shoulder recognition.

Figure 6:
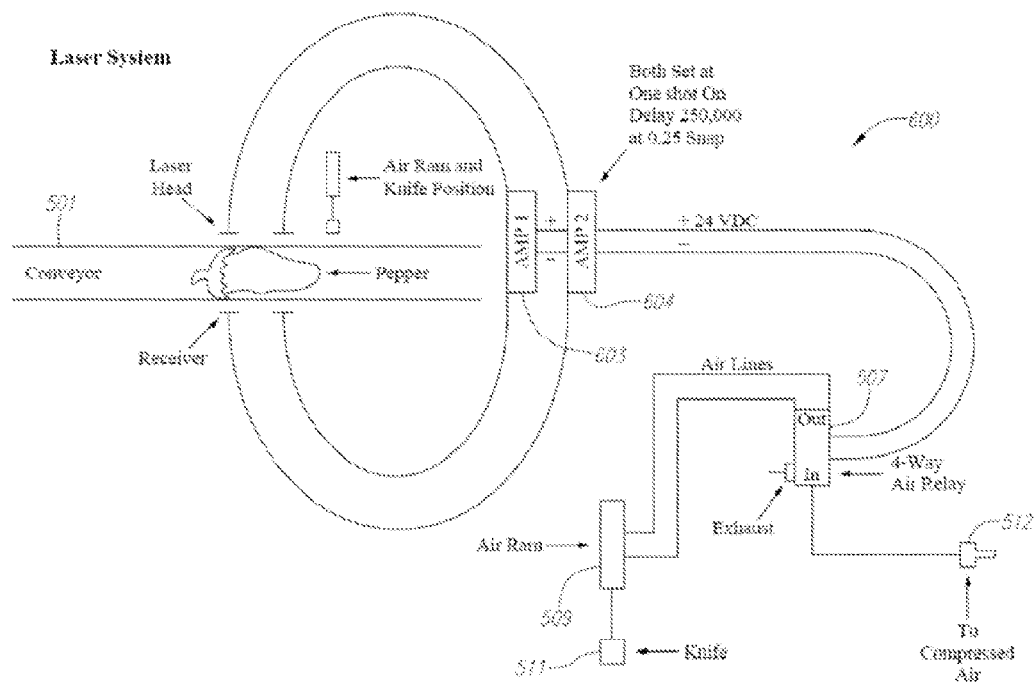

FIG. 6 is a schematic showing a second example of a pepper de-stemmer utilizing laser shoulder recognition.

Figure 7:
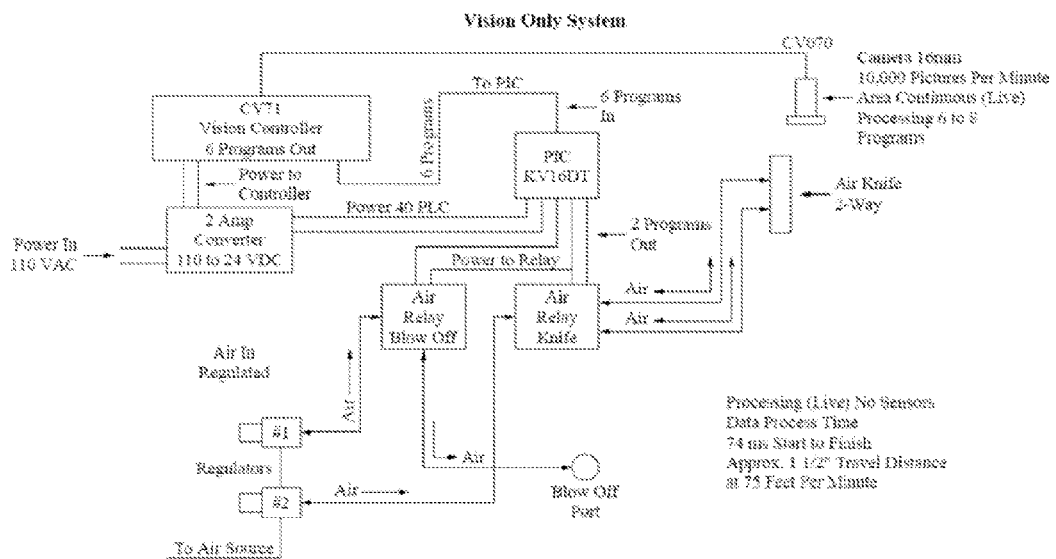

FIG. 7 is a schematic showing a third example of a pepper de-stemmer utilizing machine vision shoulder recognition.

Figure 8:
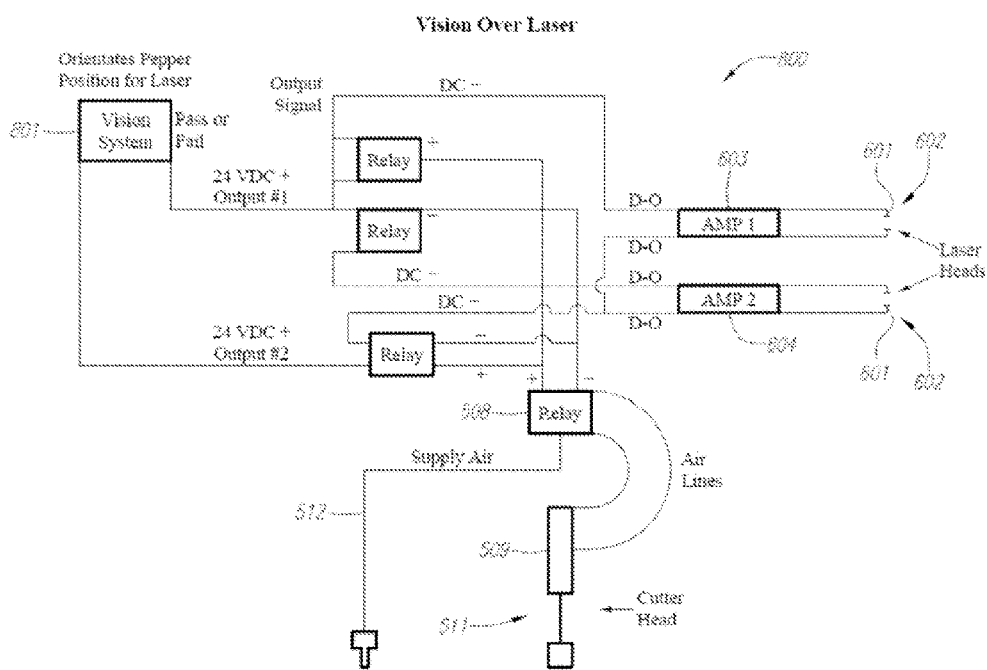

FIG. 8 is a schematic showing a fourth example of a pepper de-stemmer utilizing machine vision and laser shoulder recognition.

I. B. Processing Assembly Incorporating the Third Example of a Pepper De-Stemmer (Machine Vision)

Figure 9:
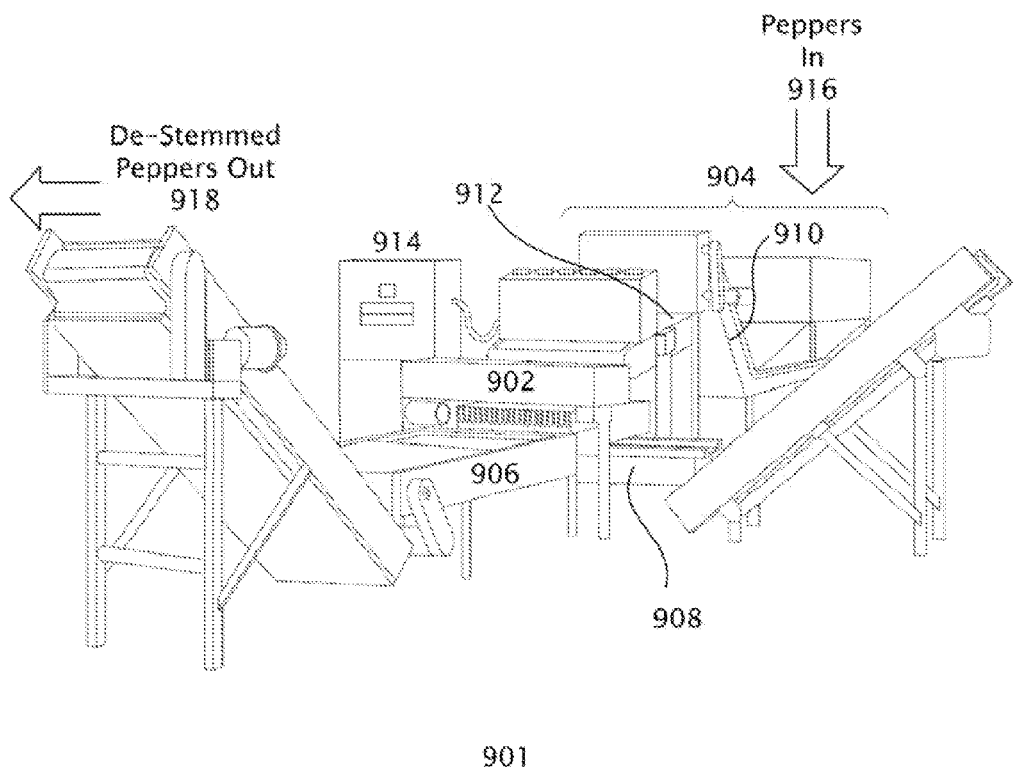

FIG. 9 shows a perspective view of an second example of a pepper de-stemming processing assembly utilizing machine vision shoulder recognition.

Figure 10:
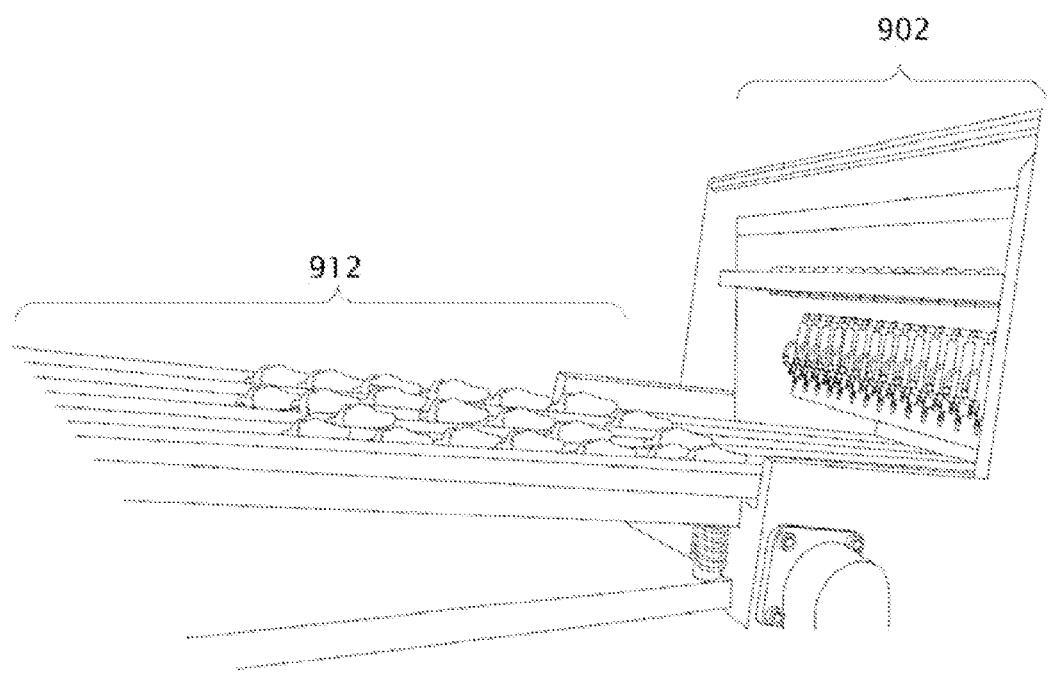

FIG. 10 shows a side view of the second example of a pepper de-stemming processing assembly utilizing machine vision shoulder recognition.

I. C. Processing Assembly Incorporating the Second Example of a Pepper De-Stemmer (Laser)

Figure 11:
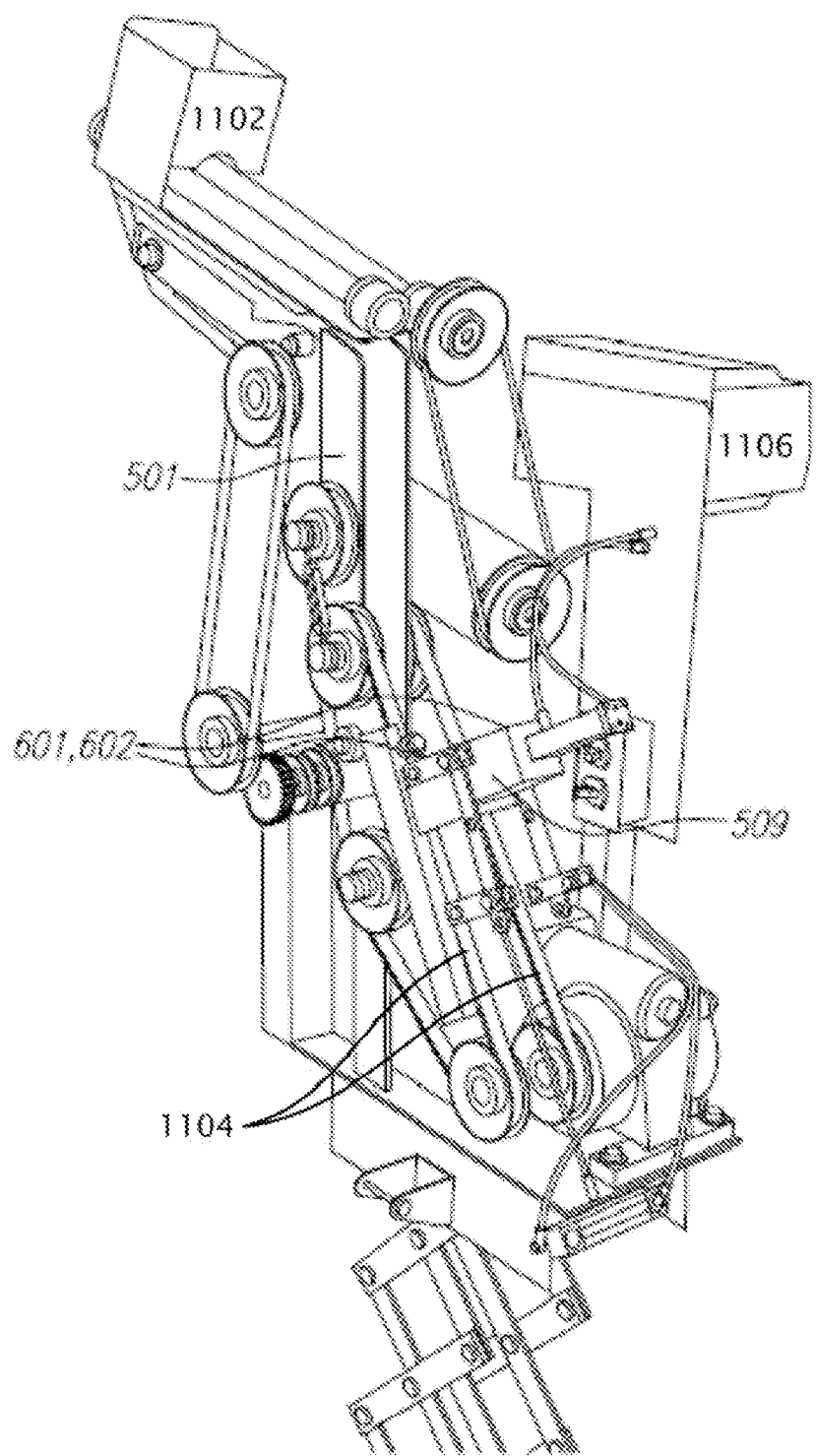

FIG. 11 shows a assembly view of an early example of a single lane pepper de-stemming machine utilizing the second example of laser shoulder recognition.

Figure 12:
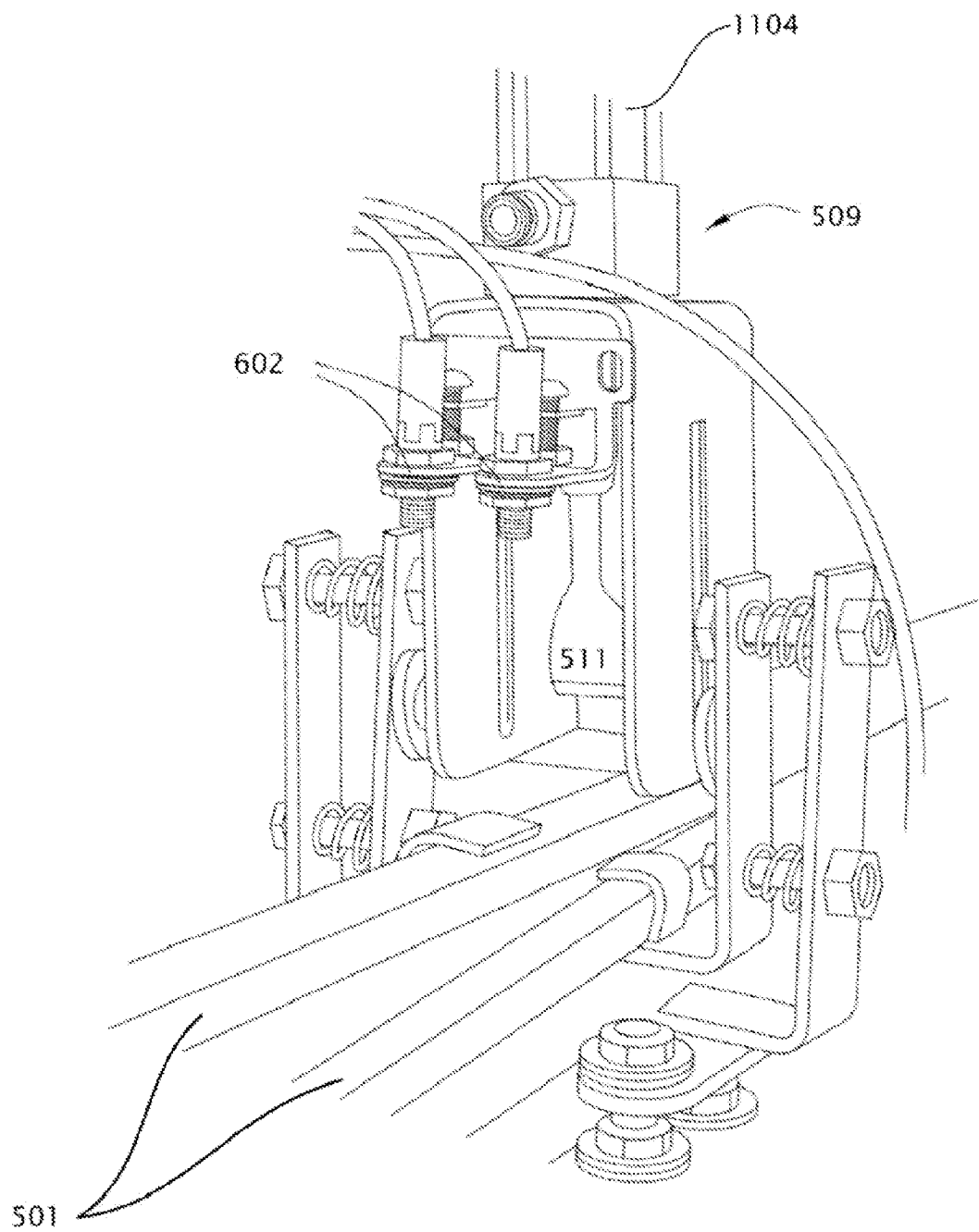

FIG. 12 shows further detail of the assembly view of an early example of a single lane pepper de-stemming machine utilizing the second example of laser shoulder recognition.

II. Assembly of Modular De-Stemmers and Processing Plant Layout

Figure 13:
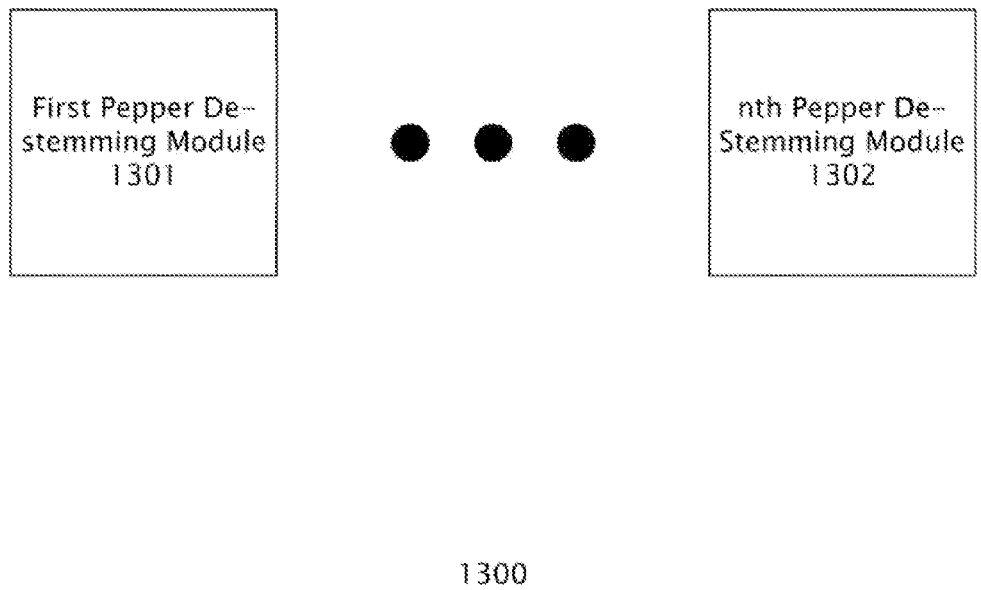

FIG. 13 shows an assembly of an example of a modularized pepper de-stemming machine into a production line for flexibility in production capacity and maintenance.

Figure 14:
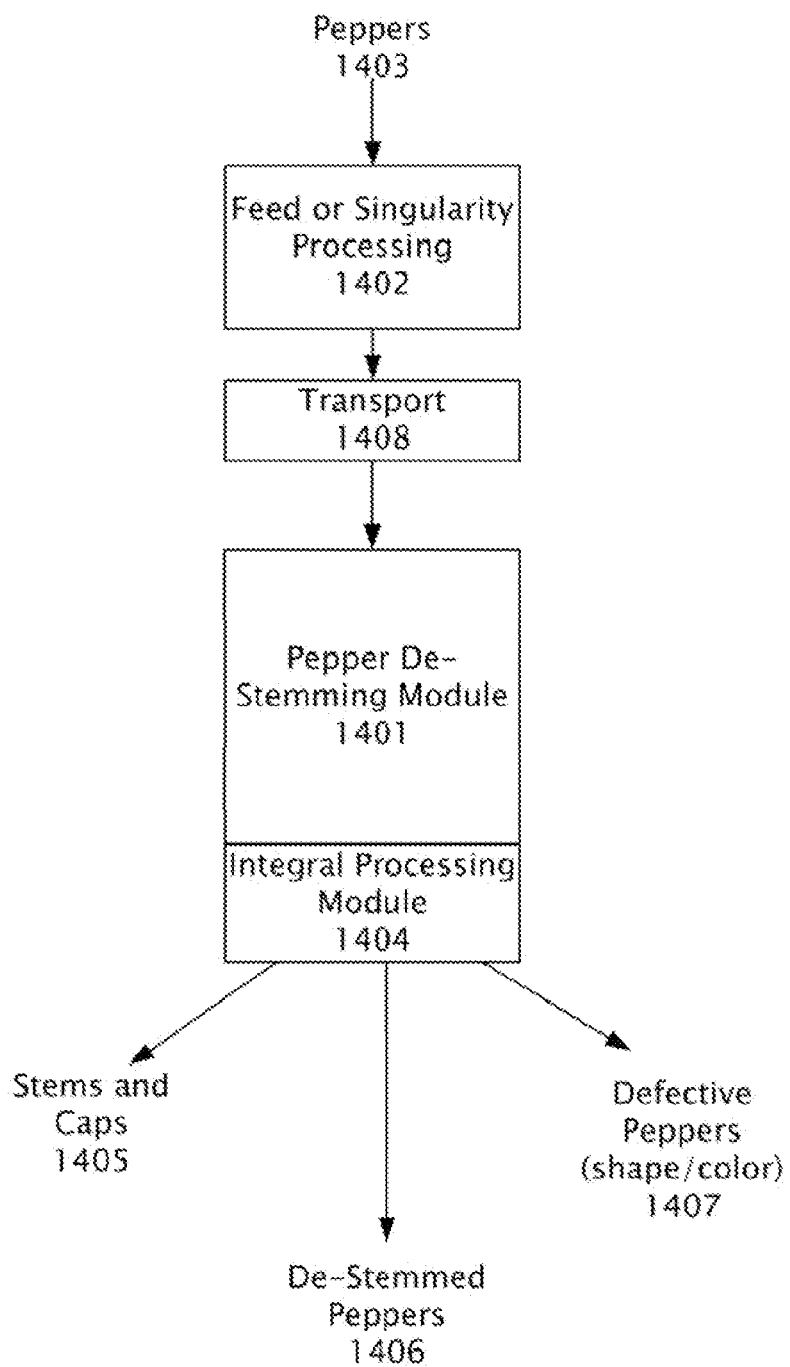

FIG. 14 shows an example of a pepper de-stemmer working in conjunction with additional components for processing whole peppers such as singularity processing, grading whole peppers and the like.

Figure 15:
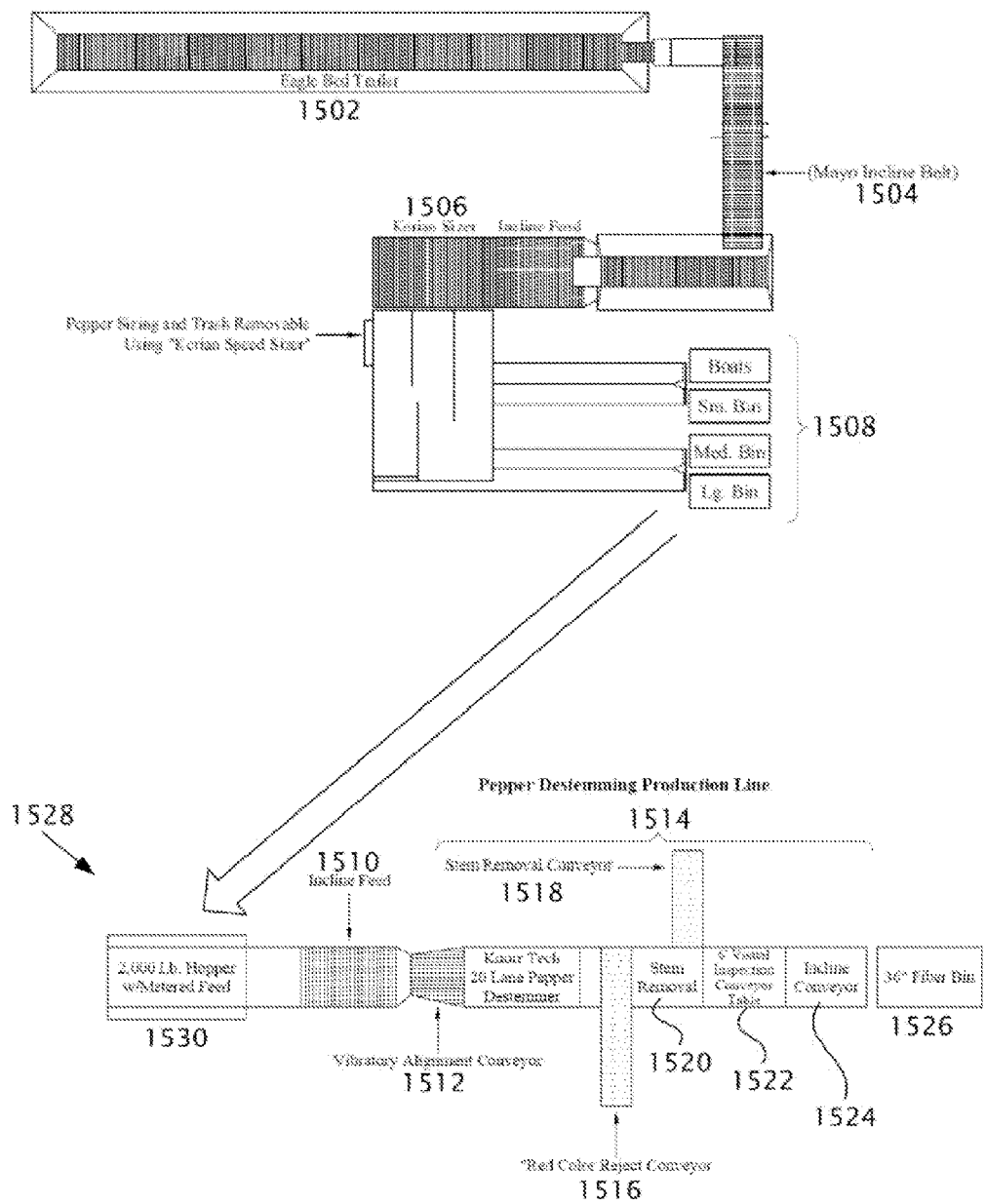

FIG. 15 shows a floor plan for a pepper processing facility utilizing pepper de-stemming machinery.

Figure 16:
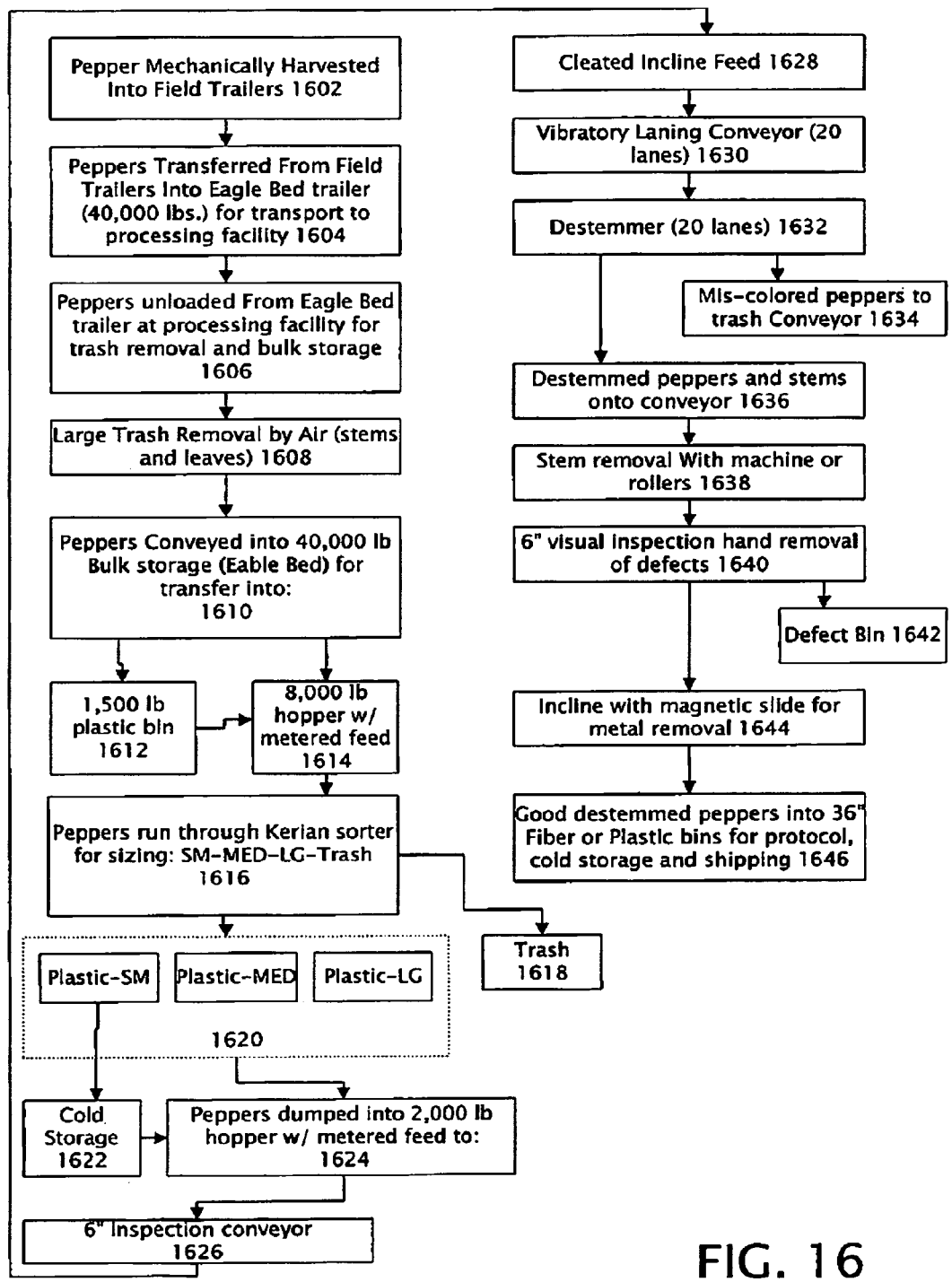

FIG. 16 is a flow diagram showing pepper processing in a facility utilizing pepper de-stemming machinery.

III. General Processor Description

Figure 17:
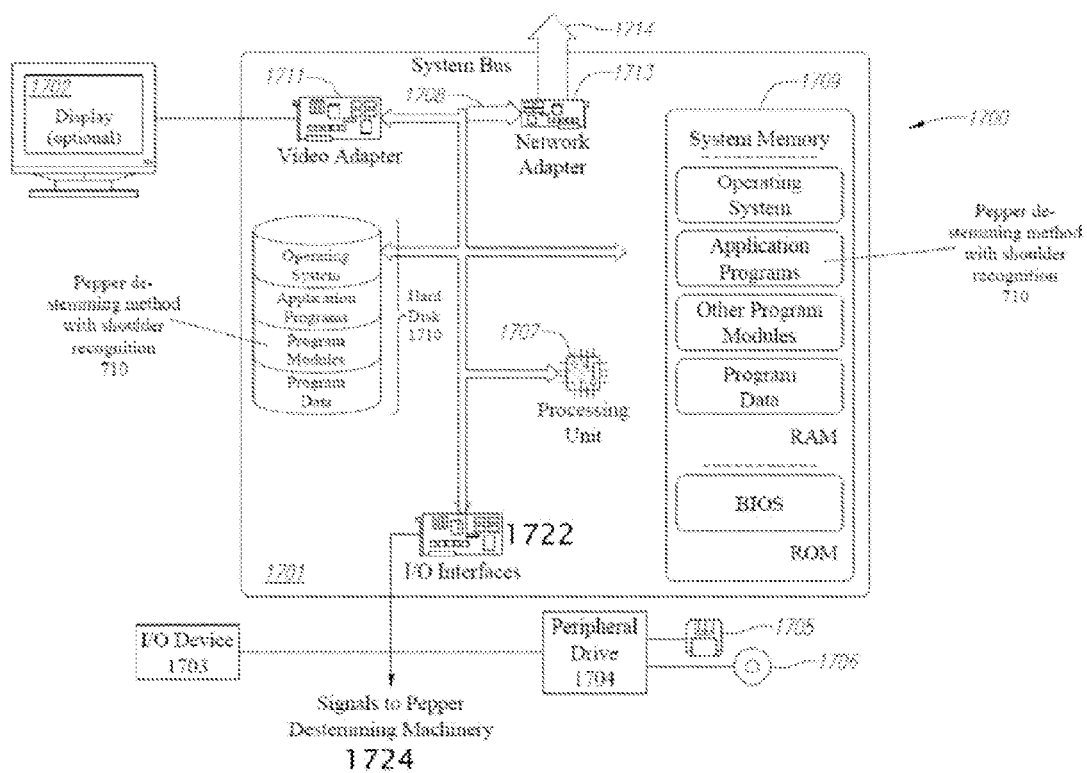

FIG. 17 is a block diagram of a computer system for providing control signals for implementing a method of de-stemming a pepper utilizing mechanical, or laser, shoulder recognition.

IV. Cutting Assembly with Hold Down

Figure 18:
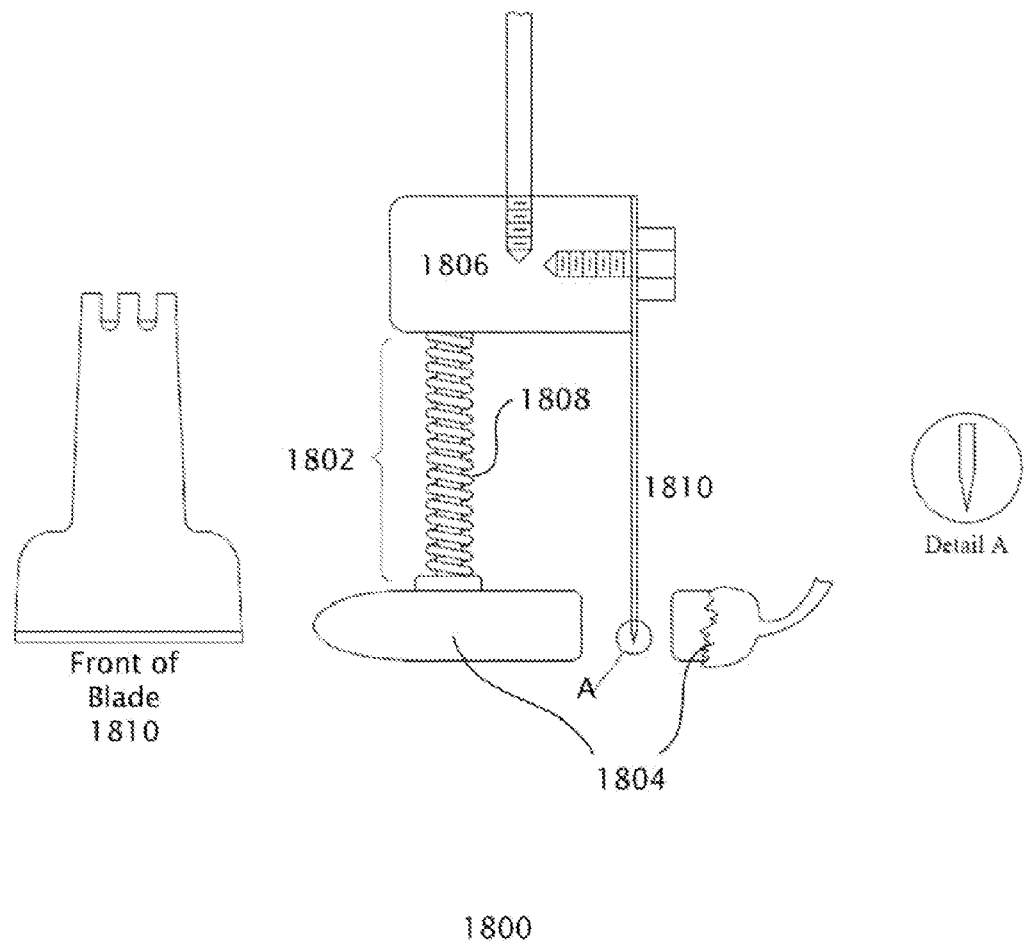

FIG. 18 shows a cutting assembly with a hold down to keep the pepper from flipping when cut.

V. Further Detail of the Third Example of a Pepper De-Stemmer (Machine Vision)

Figure 19:
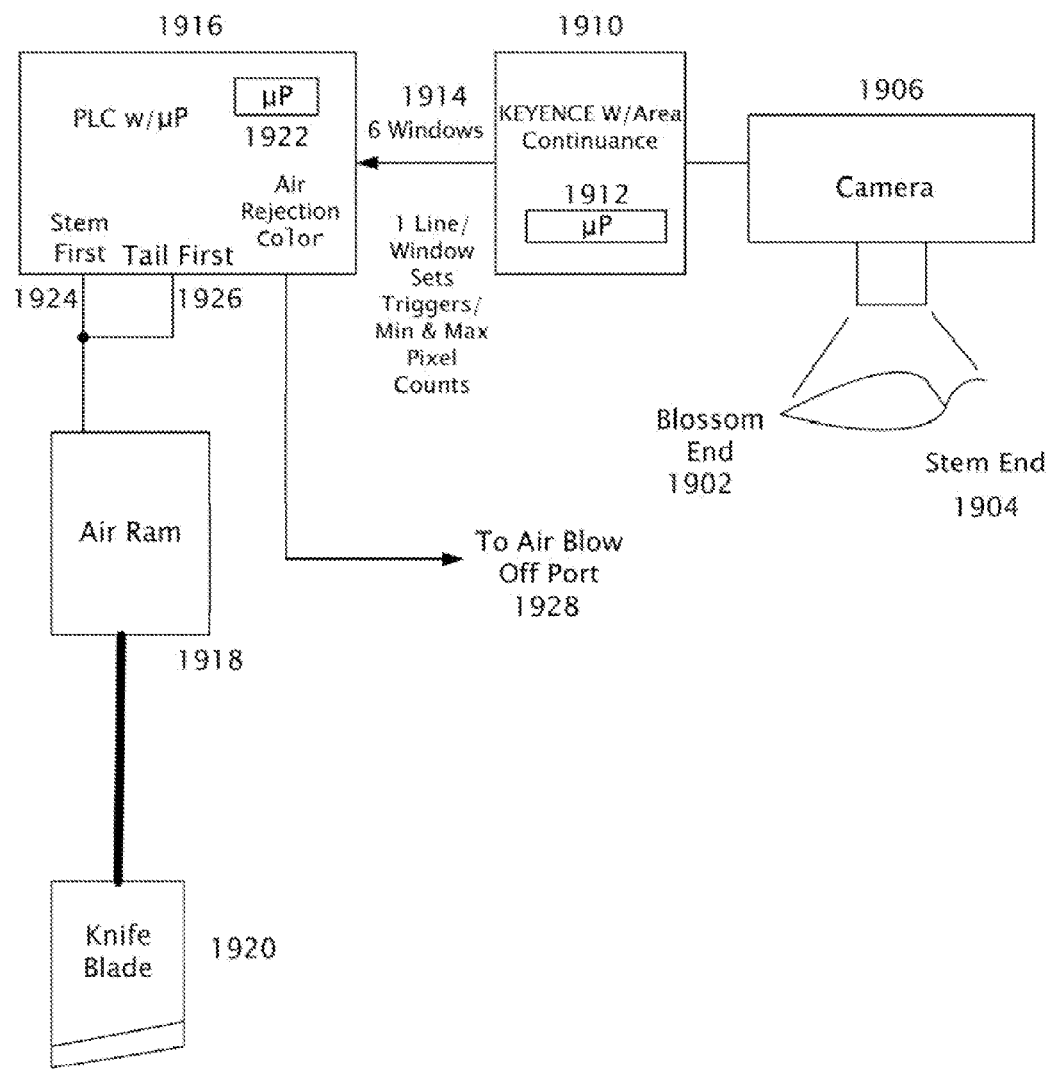

FIG. 19 shows further detail of a vision system implementing the third example of a pepper de-stemmer utilizing machine vision shoulder recognition.

Figure 20:
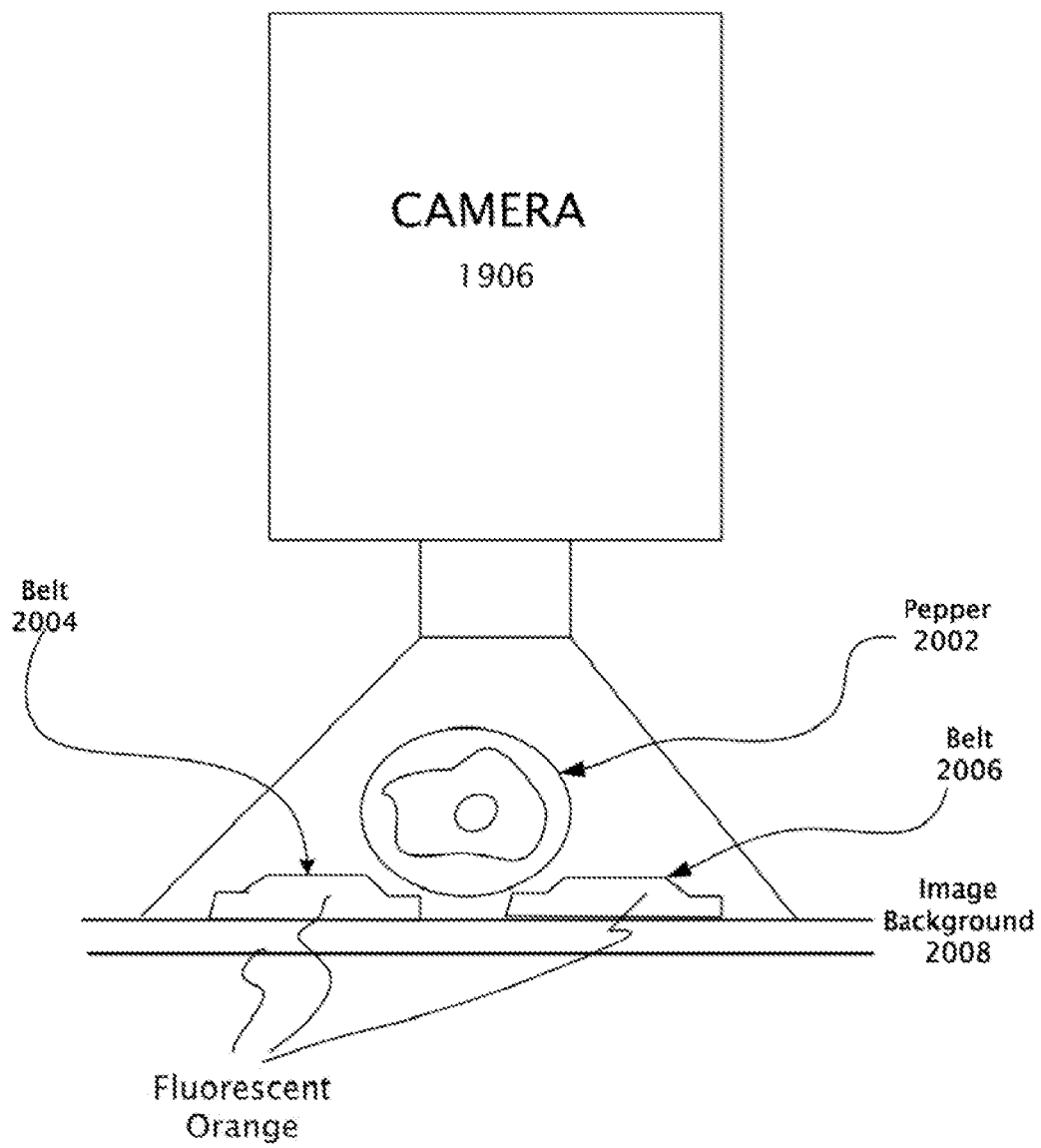

FIG. 20 shows an end view of a pepper resting on drive belts used to transport it along a production line during processing.

Figure 21:
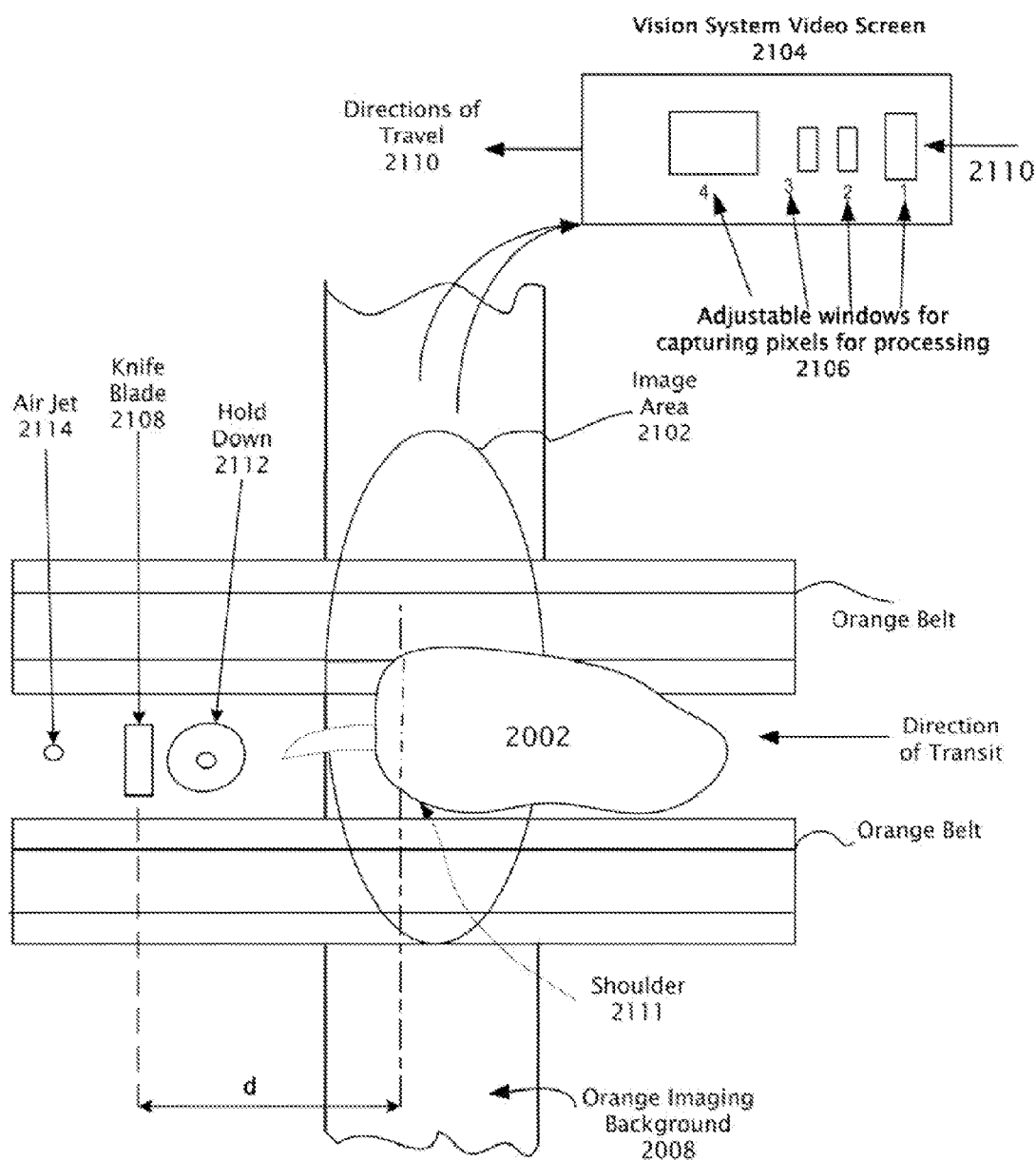

FIG. 21 shows an overhead view of a pepper traveling along a production line that will be de-stemmed using the method of shoulder recognition.

Figure 22:
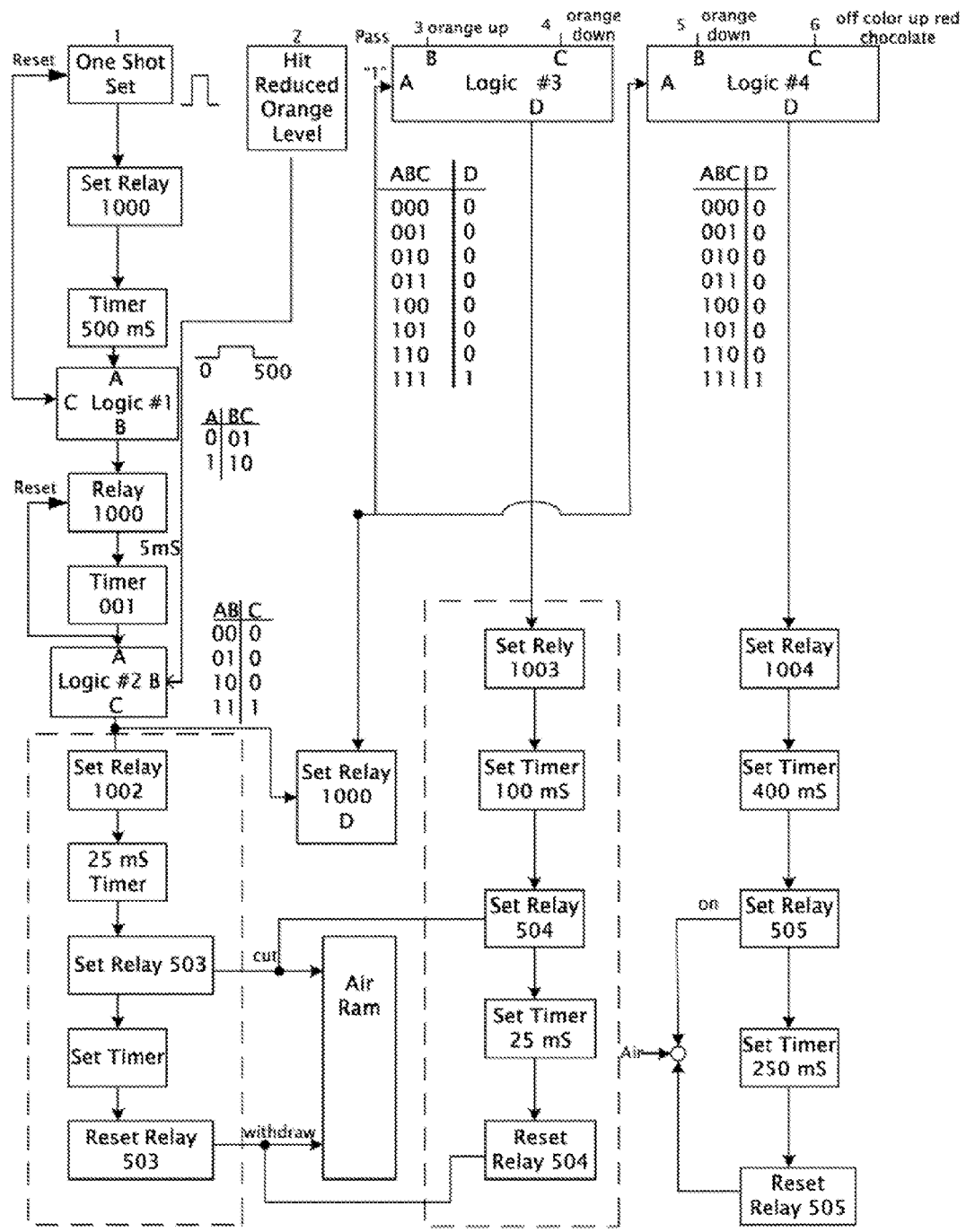

FIG. 22 is a process flow diagram showing a sequence of steps to control the PLC of the de-stemmer machine of FIG. 19.

Figure 23:
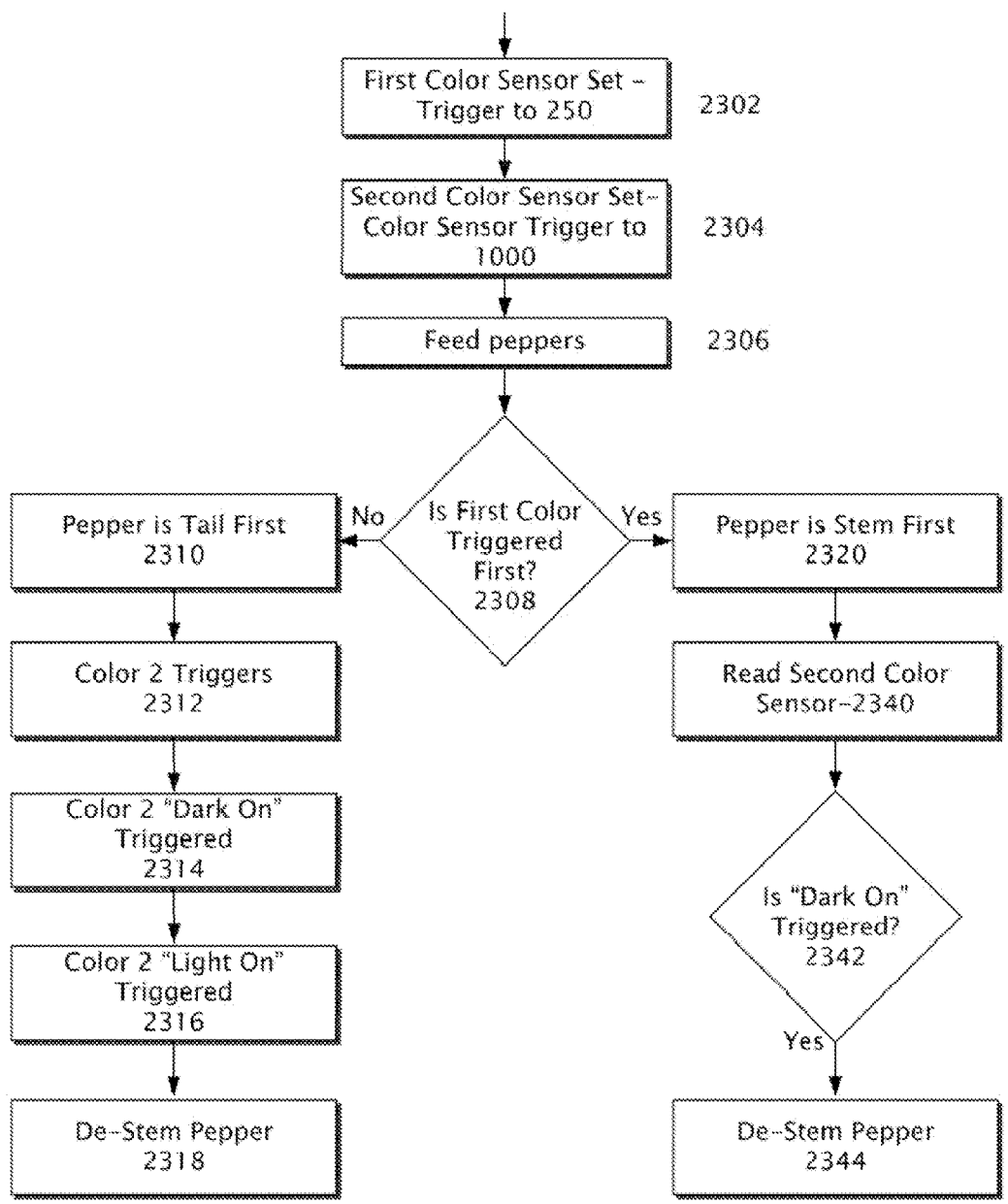

FIG. 23 is a generalized process flow diagram of the de-stemmer example shown in FIG. 19.

VI. De-Stemming Based on Evaluation of the Interior

VI. A. Processing Assembly with Infrared De-Stemmer

Figure 24:
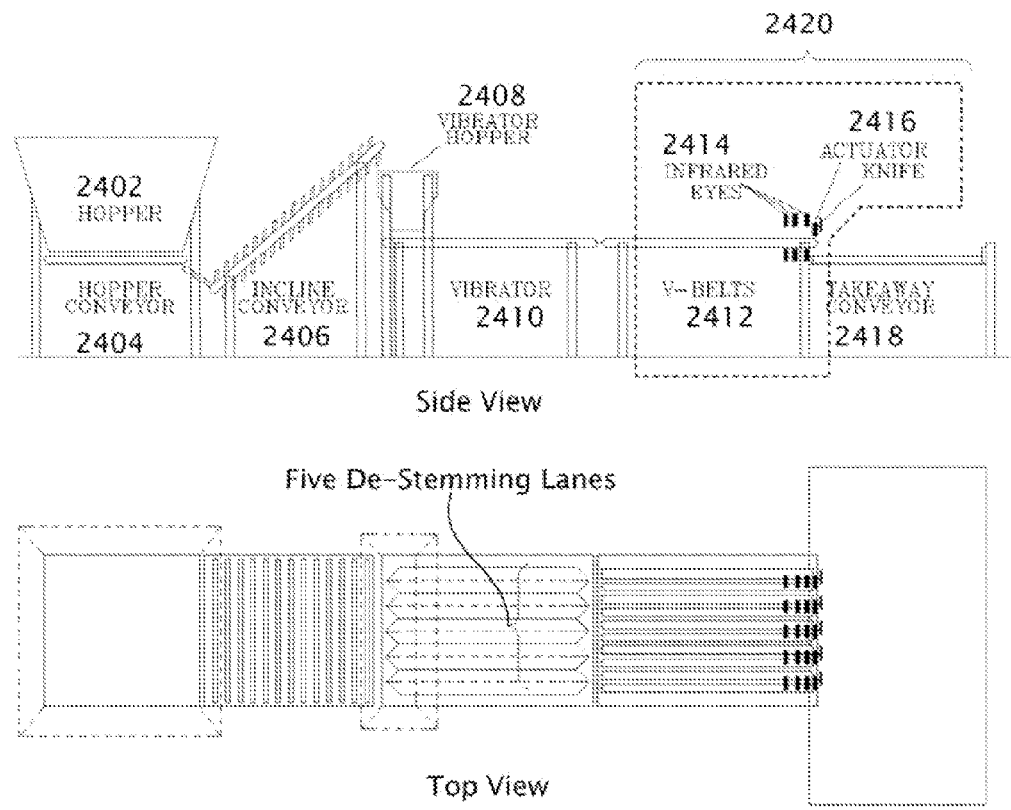

FIG. 24 is a diagram of processing machinery that inputs harvested peppers and produces peppers that are de-stemmed by an example of a de-stemmer machine disposed in the processing machinery.

Figure 25:
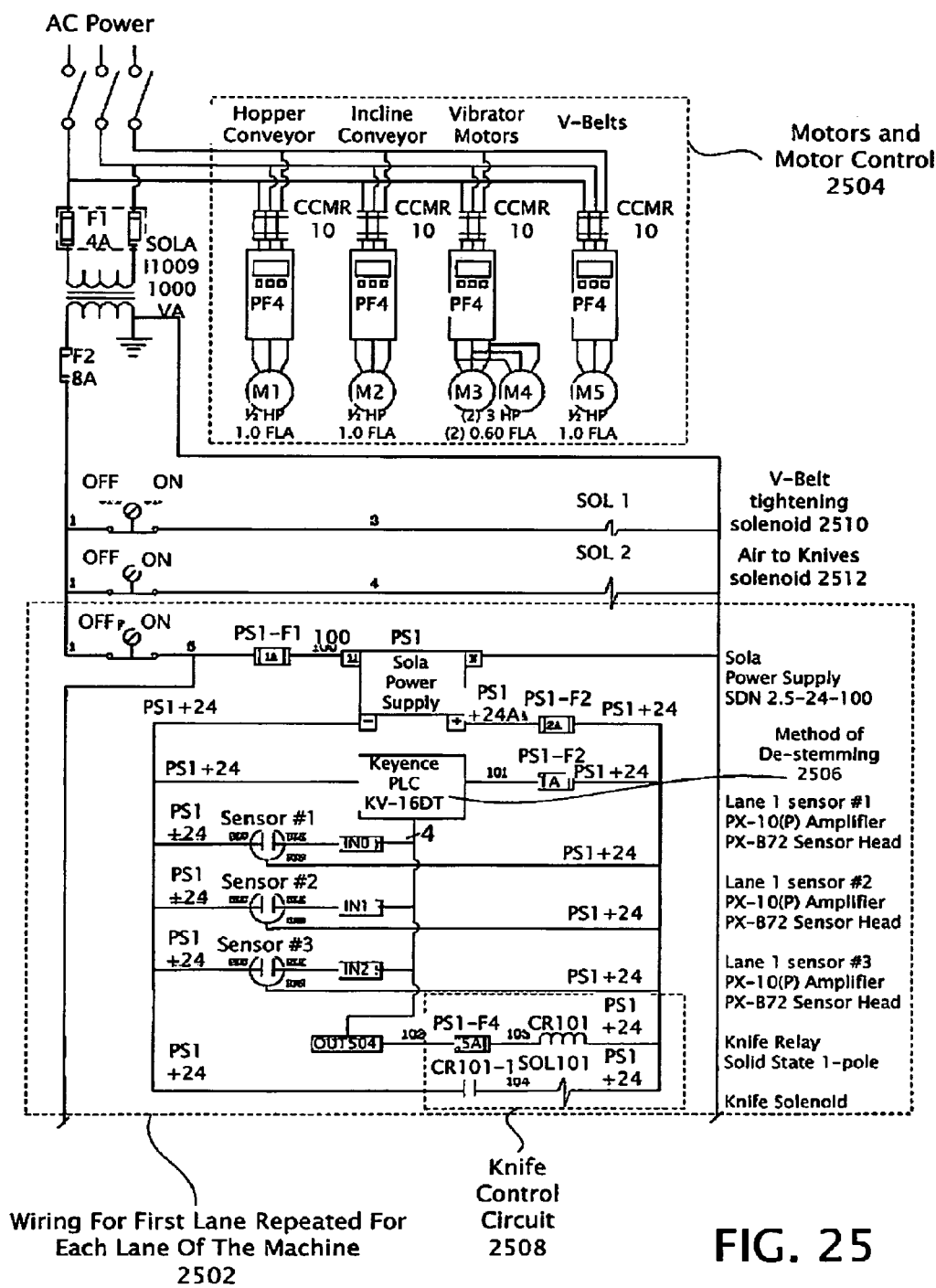

FIG. 25 is a schematic diagram of the de-stemmer machine, including the configuration of a single processing lane.

Figure 26:
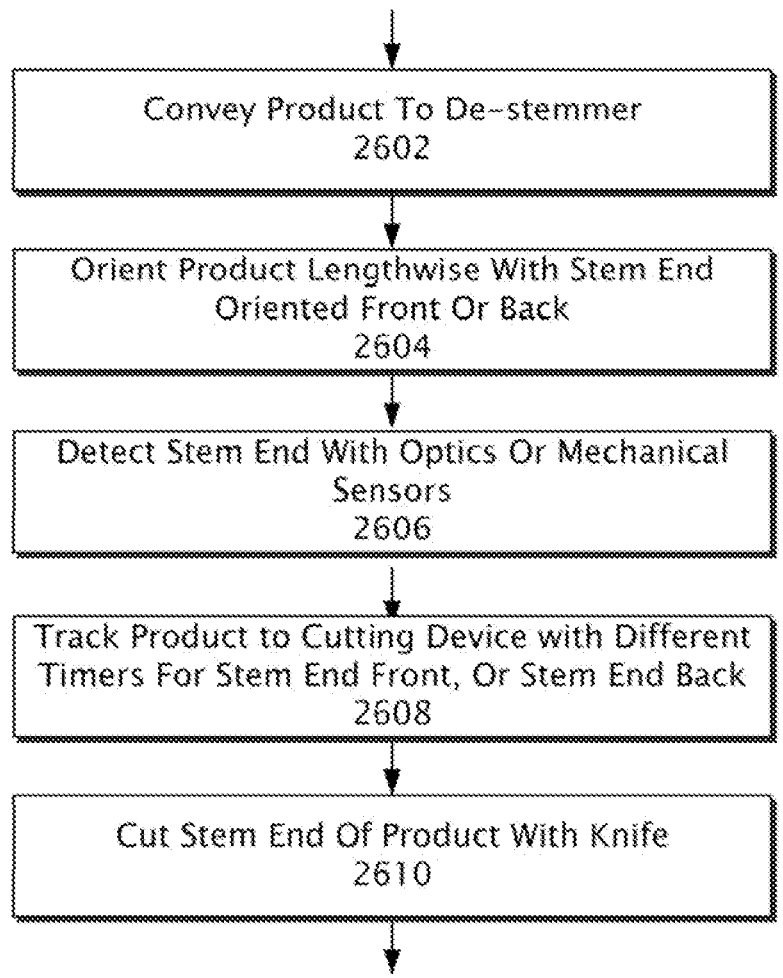

FIG. 26 is a process flow diagram showing a generalized method for de-stemming peppers.

Figure 27:
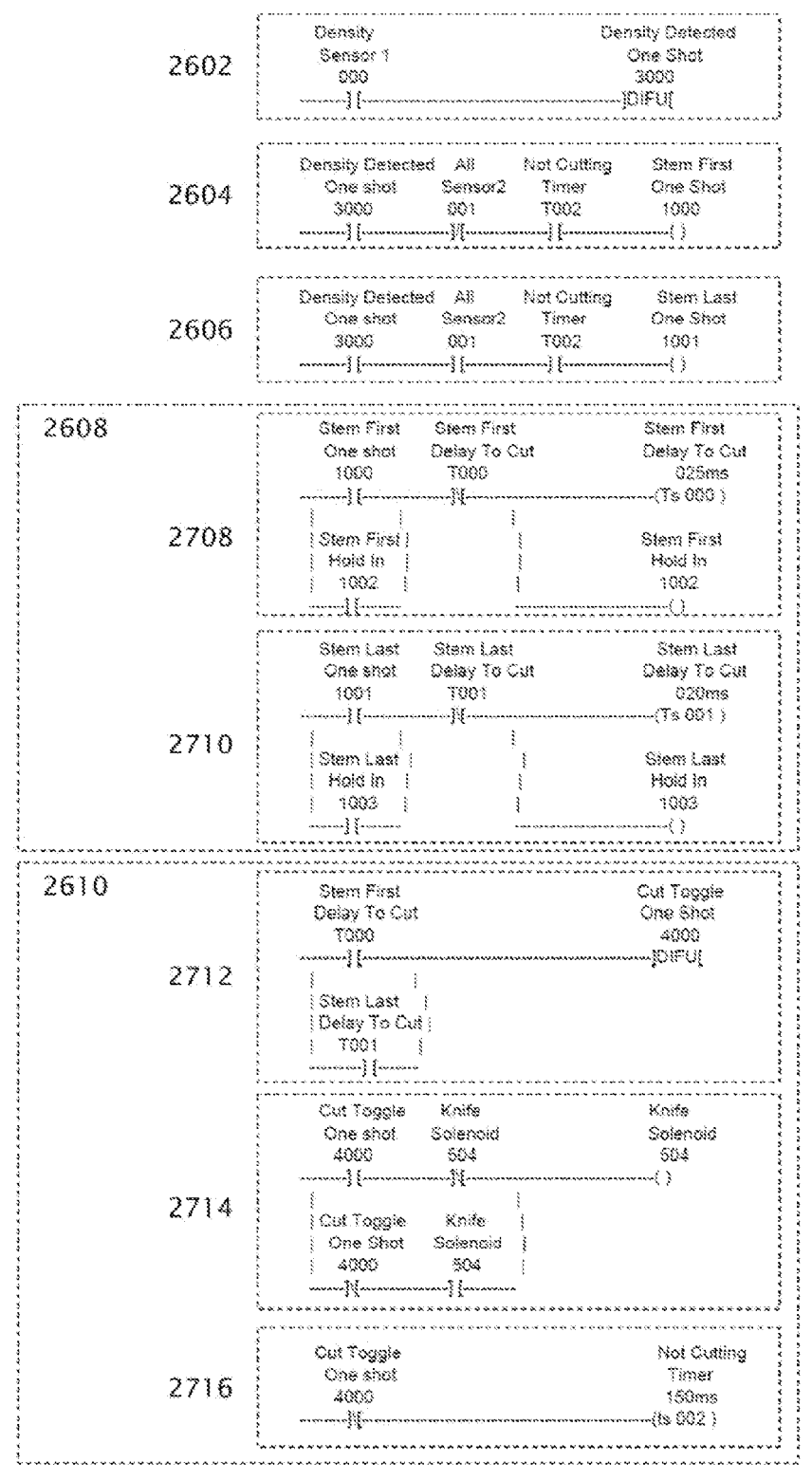

FIG. 27 is a process flow diagram showing details of an example of a generalized method for de-stemming peppers that employs two infrared sensors.

VI. B. Processing Assembly with Infrared De-Stemmer

Figure 28:
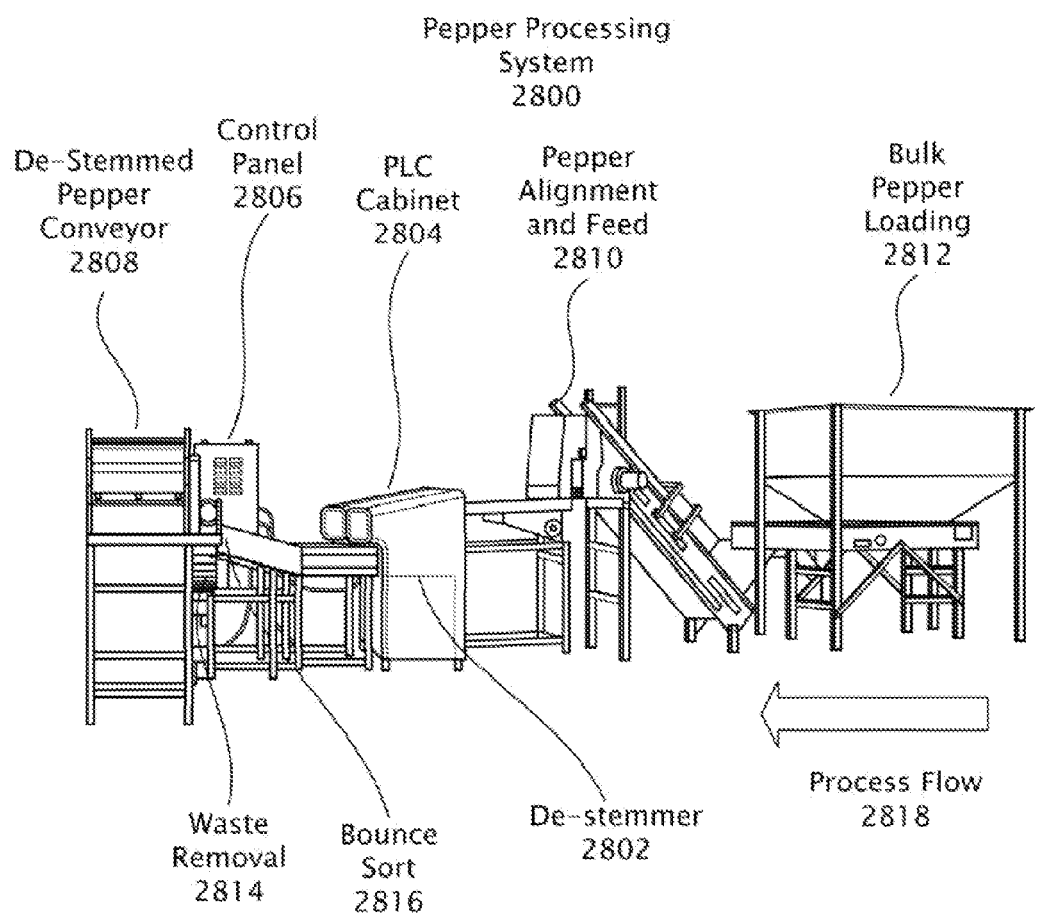
Figure 28:
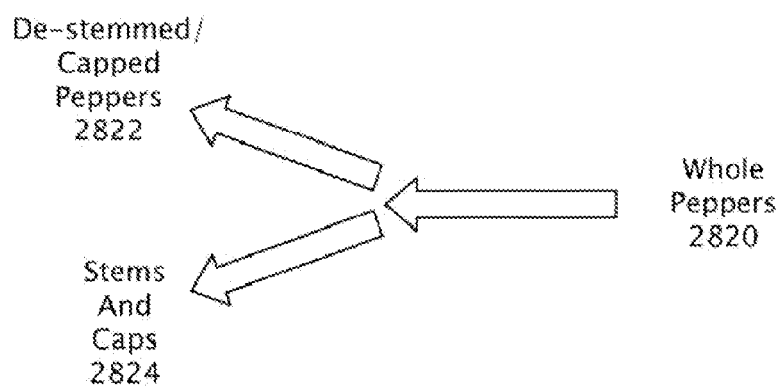

FIG. 28 is a diagram processing machinery including an example of a pepper de-stemming machine that utilizes side mounted sensors and a bounce sorter to separate the stems from the de-stemmed peppers.

Figure 29:
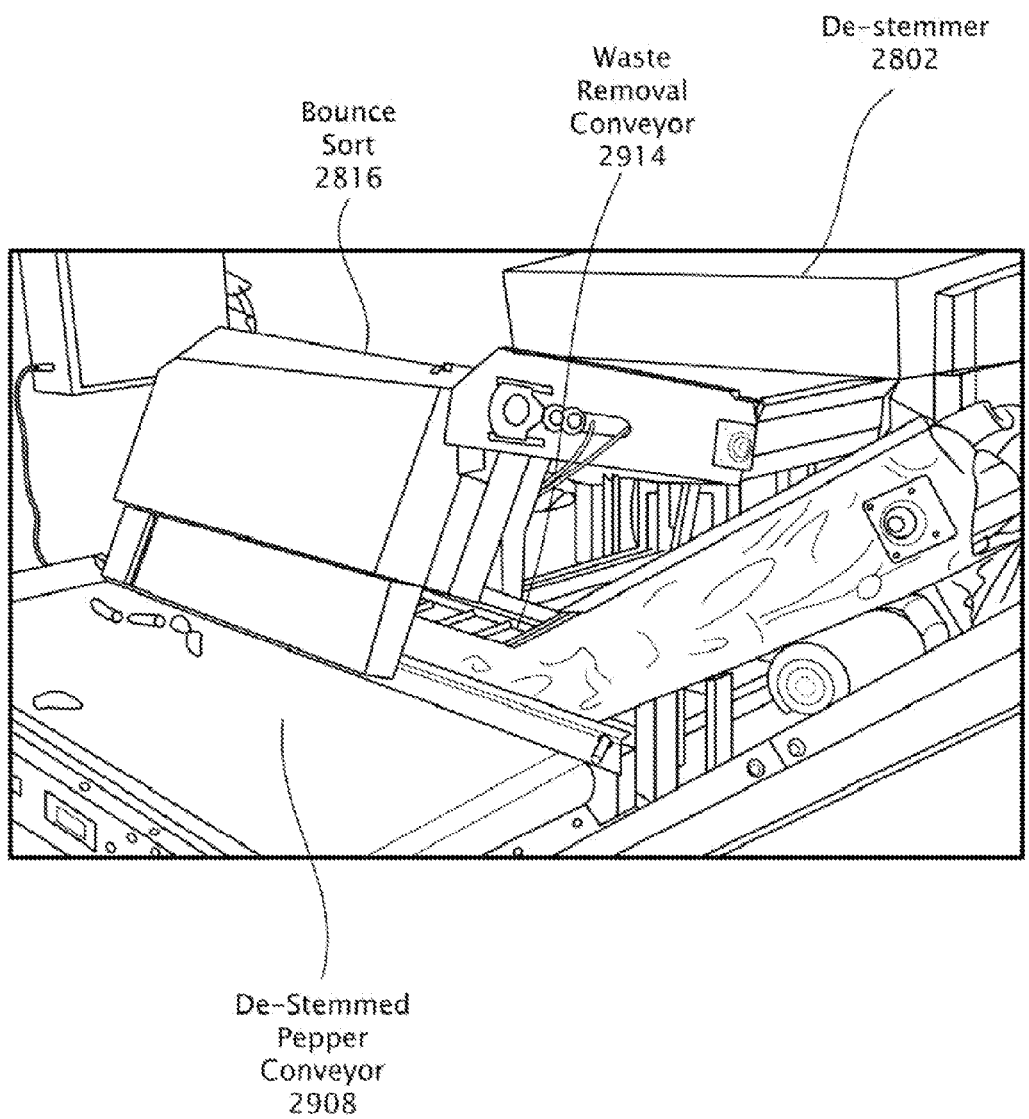

FIG. 29 is a diagram of a de-stemmer machine utilized in FIG. 28.

Figure 30:
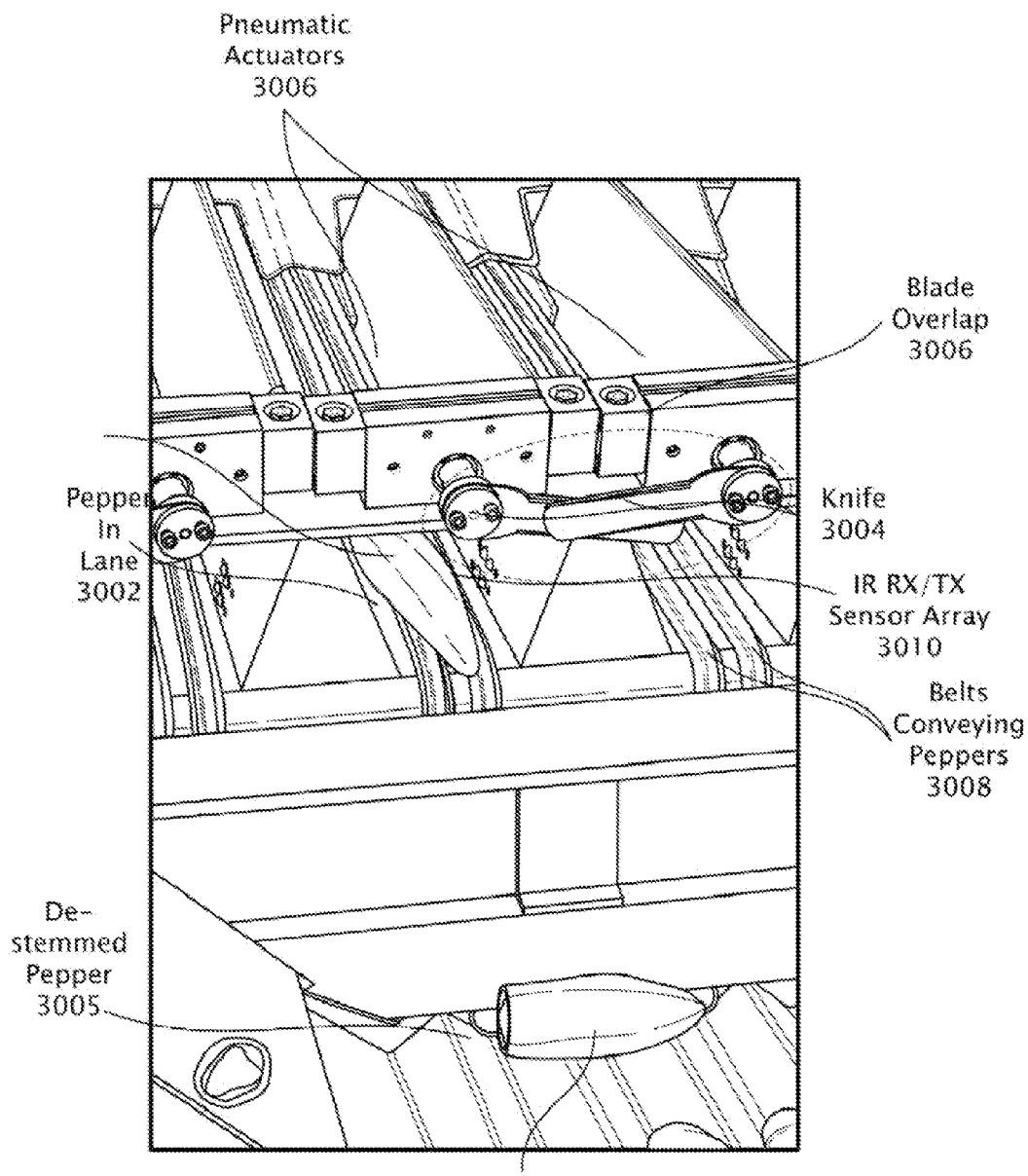

FIG. 30 is a diagram showing peppers being carried through an example of a de-stemmer machine.

Figure 31:
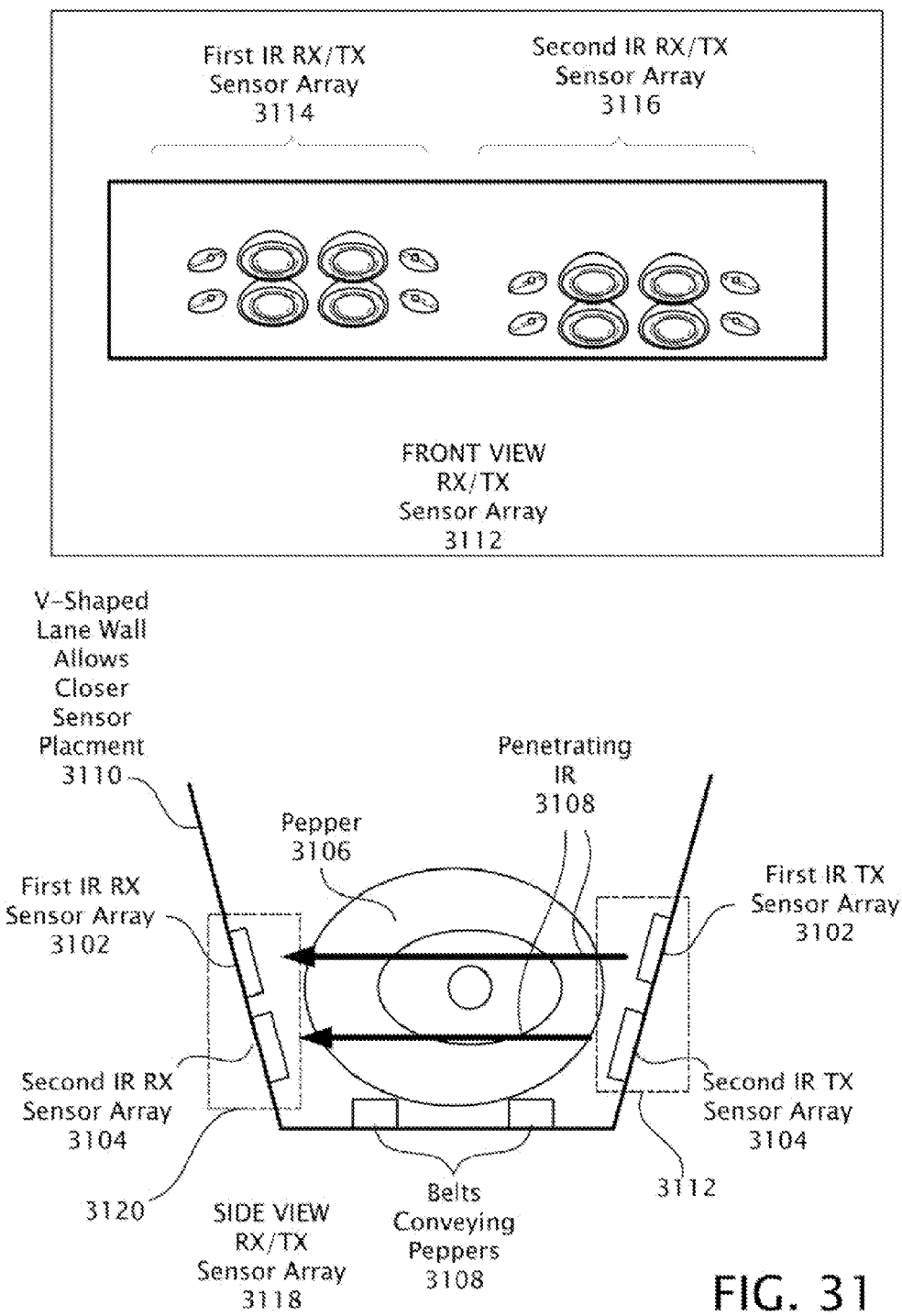

FIG. 31 shows an example of a de-stemmer machine sensor array disposed in the side walls of a de-stemmer lane (vertical sensor disposition).

Figure 32:
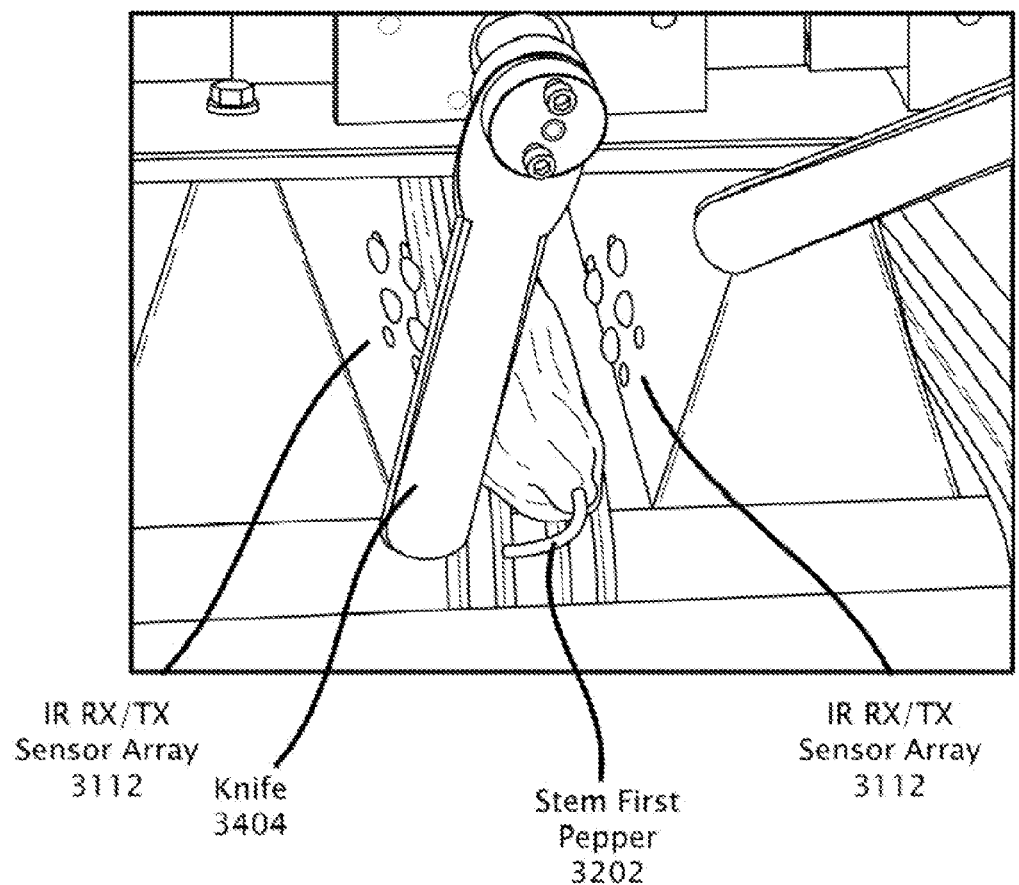

FIG. 32 shows a pepper being de-stemmed as it enters an example of the de-stemmer machine stem first.

Figure 33:
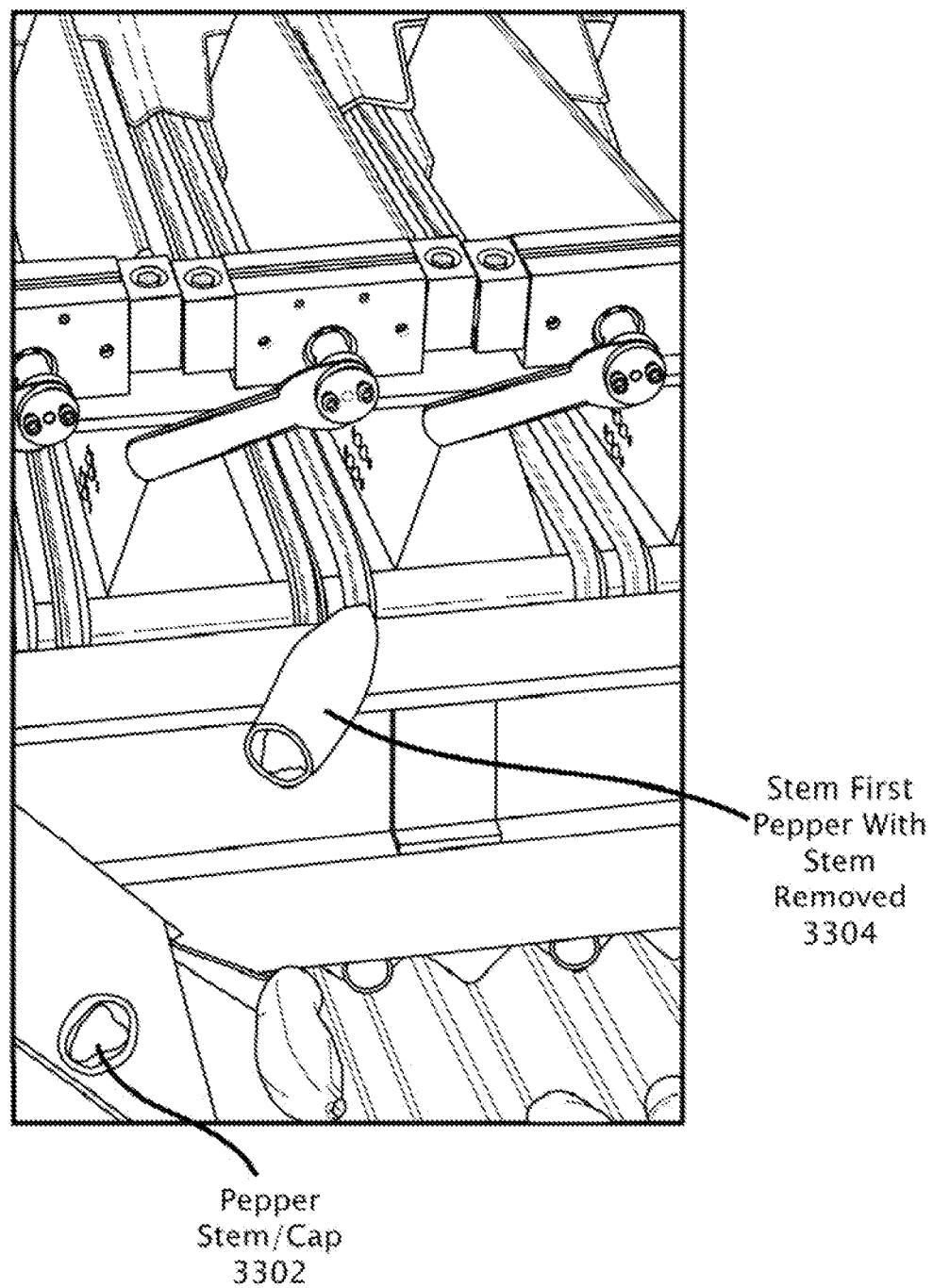

FIG. 33 shows a de-stemmed pepper as it leaves an example of the de-stemmer machine tail last.

Figure 34:
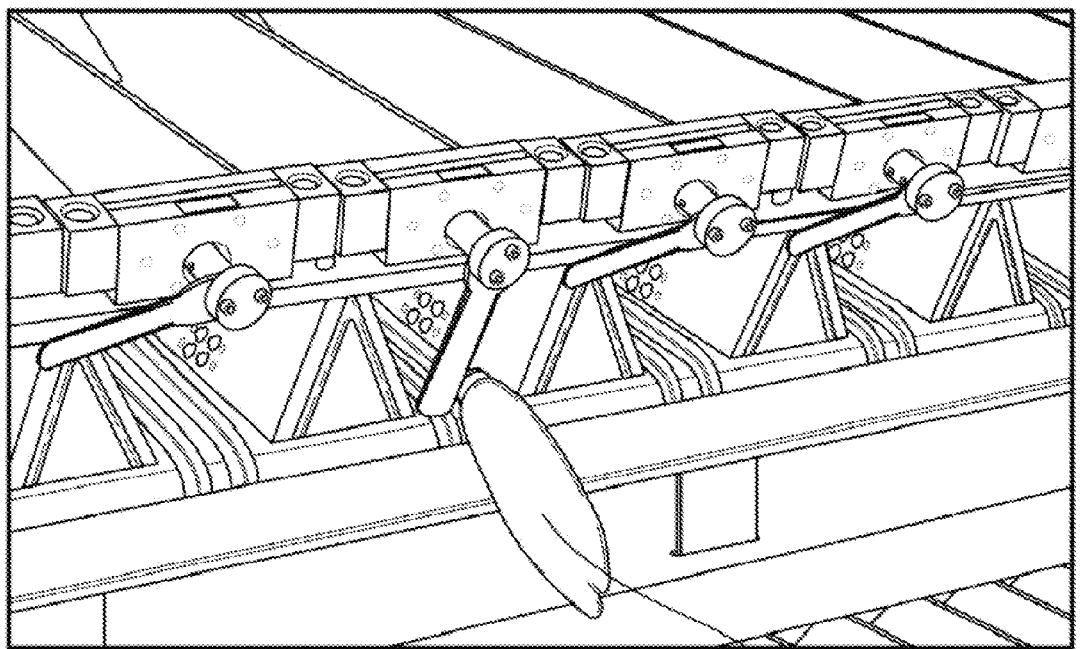

FIG. 34 shows a pepper being de-stemmed as it enters an example of the de-stemmer machine tail first.

Figure 35:
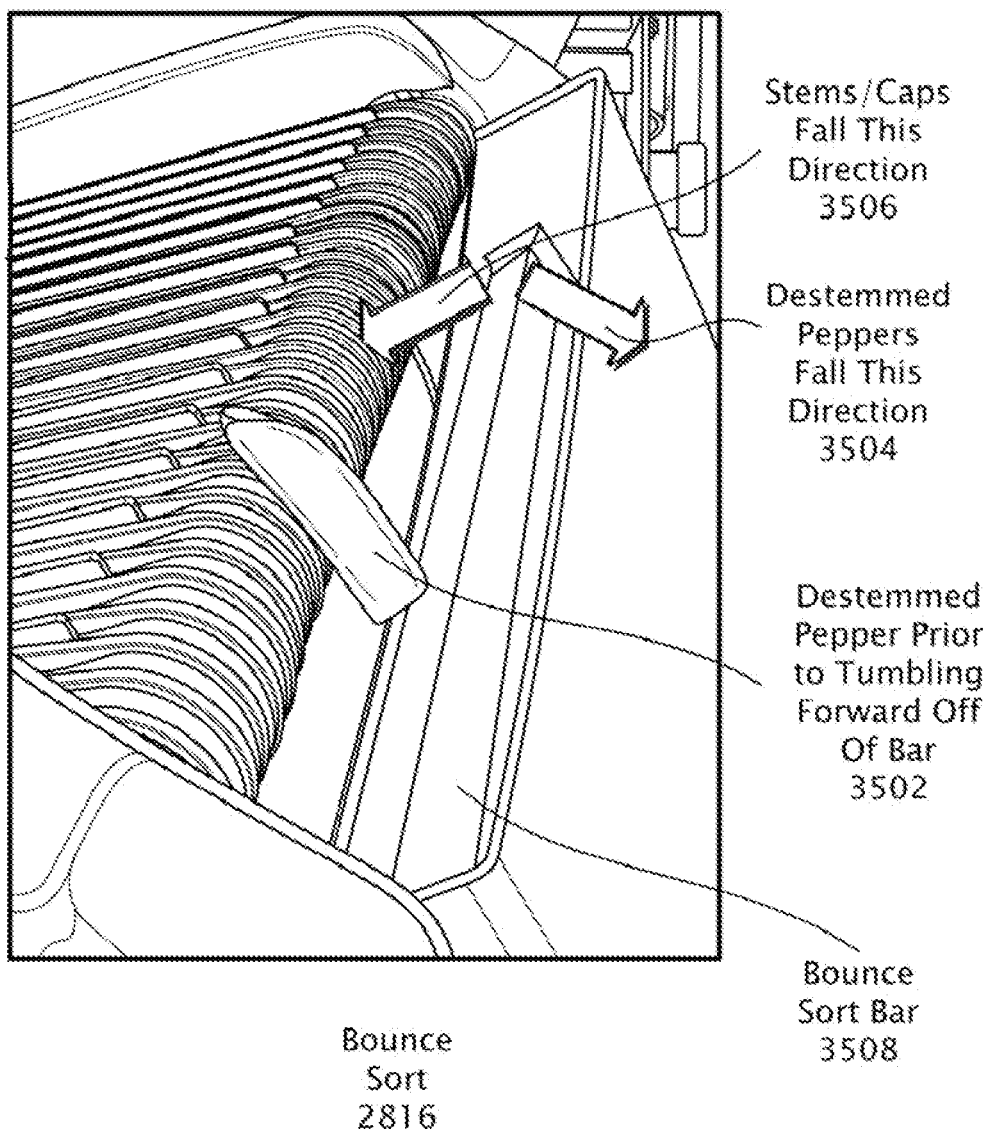

FIG. 35 shows an example of a bounce sorting machine for separating de-stemmed peppers from the stems.

Like reference numerals are used to designate like parts in the accompanying drawings.

DETAILED DESCRIPTION

Whole pepper de-stemming as used in this document is defined as the process of removing the stem, calyx and the woody tissue associated with the stem and the calyx. De-stemming of this type is typically aimed at producing a remaining pepper pod that has the previously mentioned items removed, without removing so much material that the cavity of the pepper is opened to outside air. Intrusion of air in the pepper lobes tends to promote bacteria growth, causing pepper decay. Thus, it is desirable to leave enough of the placenta to seal the pepper lobe when de-stemming. De-stemming in this manner tends to increase the shelf life of the peppers, in part because of a reduced respiration with this type of de-stemming where a portion of the placenta may remain after de-stemming that tends to seal the interior of the pepper, but removes the woody stem. On the exterior of a typical pepper starting at the shoulder, moving towards the Apex (or blossom end), the width of the pepper typically decreases on both sides of the pod. At the apex end of the pepper opposite the stem, the pepper may curl to one side. However, the methods described below are typically insensitive to these irregularities in shape. When an examining signal or signals passes through the pepper, it is worth noting that the stem tends to have increased density over the other parts of a pepper, and the placenta area with the seeds tends to be denser than many other parts of a pepper which may further aid in determining where to place a cut to de-stem a pepper.

This disclosure describes methods of de-stemming peppers, other vegetables and fruits implemented in examples of pepper de-stemming machines that utilize shoulder recognition, and or recognition of the placenta to identity and the shoulder and subsequently remove the stem and calyx of a whole pepper. Recognition of these areas may be accomplished by examining the exterior of the pepper, or by illuminating the pepper with an electromagnetic signal and examining its shadow or the strength of the signal not absorbed by the pepper. As used in this application a whole pepper generally refers to a pepper in its "as-picked" condition from the field. Shoulder recognition, and or recognition of the placenta can be implemented by various mechanical, electrical, or optical systems. The whole peppers that may have their stems and calyx removed, include jalapeño's, long green Anaheim chili peppers, and in general all varieties of peppers. Additionally other types of fruits and vegetables having stems, shoulders, and or placentas may be de-stemmed using the methods described herein. The examples provided in the contest of pepper de-stemming are not intended to limit the applicability of this disclosure to peppers as the devices and methods herein are widely applicable to a variety of fruits and vegetables. The de-Stemmer machine implements a method of de-stemming to typically recognizes the shoulder, and or placenta of a pepper, determines where to place a cut, cuts off the stem and calyx, and transports the pepper for further processing. Various methods of de-stemming and apparatuses for de-stemming peppers may be implemented. In particular two categories of de-stemming may be observed, de-stemming by examining the exterior, and de-stemming by examining the interior.

In exterior examples of FIGS. 3-12 and FIGS. 19-23 of recognizing a shoulder of a pepper by switches, lasers vision systems (or equivalently termed herein as an area continuance vision system, or real time processing vision system) may be used. In the system of FIGS. 19-23 the general vision system of FIG. 7 is expanded upon that captures images of passing peppers and processes them to determine the shoulder of the pepper and remove the calyx at the appropriate time.

In recognizing the shoulder of the pepper, mechanical switches (FIG. 5), emitter/detector pairs (FIG. 26 and FIGS. 30-36) or machine vision systems (FIGS. 19-21) may also be used to implement shoulder recognition as described above.

In addition, a combination of a laser sensor system and machine vision system (FIG. 8) may be utilized in a further example, and in yet a further alternative example lasers may be employed (FIG. 6).

In the system of FIGS. 19-23 a pepper passes over an area of fluorescent material or other material of a suitably contrasting color. In this example the orientation of the pepper and its shoulder are recognized by examining the recorded pixels associated with the fluorescent material that are not covered by the pepper. Examination may be made on a pixel by pixel basis or by examining selectively positioned image windows.

In interior examples shown in FIG. 24-35 of de-stemmer machines, sensor pairs (typically a paired emitter and detector) capable of emitting and receiving electromagnetic waves such as visible light, infra red (IR), x-ray, microwave, radio frequency (RF), or the like may be used to illuminate a pepper to be processed that passes between the sensor pair. The placenta and or shoulder area (calyx) of the pepper tends to be denser than the tail end of the pepper. The radiation from the emitter passes through the pepper casting a shadow on the opposing sensor. The density of the placenta and or stem causes a drop in the received radiation providing an indication of where the stem or calyx area is located. Thus the orientation of the pepper can be determined, and the placenta, and or shoulder (including the denser stem) can be identified to produce a trigger signal to actuate a cutter to de-stem the pepper as it passes by the cutter.

The detailed description provided below in connection with the appended drawings is intended as a description of the present examples of a pepper de-stemmer and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe a process for de-stemming a pepper (or other vegetables). Although the present examples are described and illustrated herein as being implemented in mechanical, laser, machine vision, and laser and machine vision systems, the systems described are provided as an example and not a limitation. As those skilled in the art will appreciate, the present examples are suitable for application in a variety of different types of pepper (or other fruit and vegetable) de-stemming systems.

In the examples herein exemplary Keyence Vision System, IR Sensors (PX-872 or equivalent) and Keyence Programmable Logic Controllers (PLC KV-16DT or equivalent) made by KEYENCE CORPORATION OF AMERICA, 669 River Drive, Suite 403, Elmwood Park, N.J. 07407) with sufficient programming capabilities or their equivalents may be used. In addition to controllers of the programmable logic type, general purpose computers, programmable logic, hard wired logic and the like may be used to implement the methods described herein.

Figure 1:
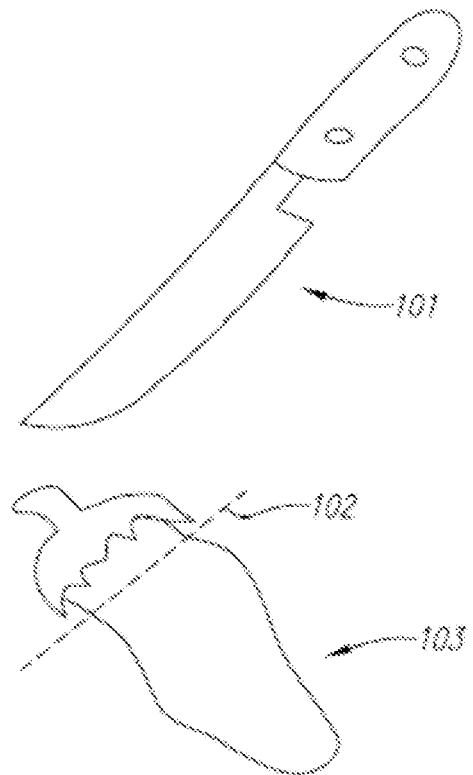
FIG. 1 shows a conventional method of de-stemming a pepper.

FIG. 1 shows a conventional method of de-stemming a pepper. A pepper 103 typically includes a cap (or calyx) and a stem that may be removed and discarded before the pepper is further processed for use in food products. Pepper processing is typically labor intensive as it is done usually with a knife or by hand. A typical method of de-stemming a pepper 103 is for a person to use a knife 101 to cut off the calyx and stem typically of each pepper at a line 102 near the calyx and stem. Alternatively a person may pull or break the stem off or calyx by hand. If labor is cheap and plentiful this method may be employed economically. However, with rising labor costs this type of work has been outsourced to producers in other countries. Discovering a better method of de-stemming peppers that can be done close to the grower and consumer tends to promote a fresh product produced economically and locally. In addition peppers that have been mechanically processed may have less chance of being contaminated, since fewer human hands have touched the pepper or product.

Figure 2:
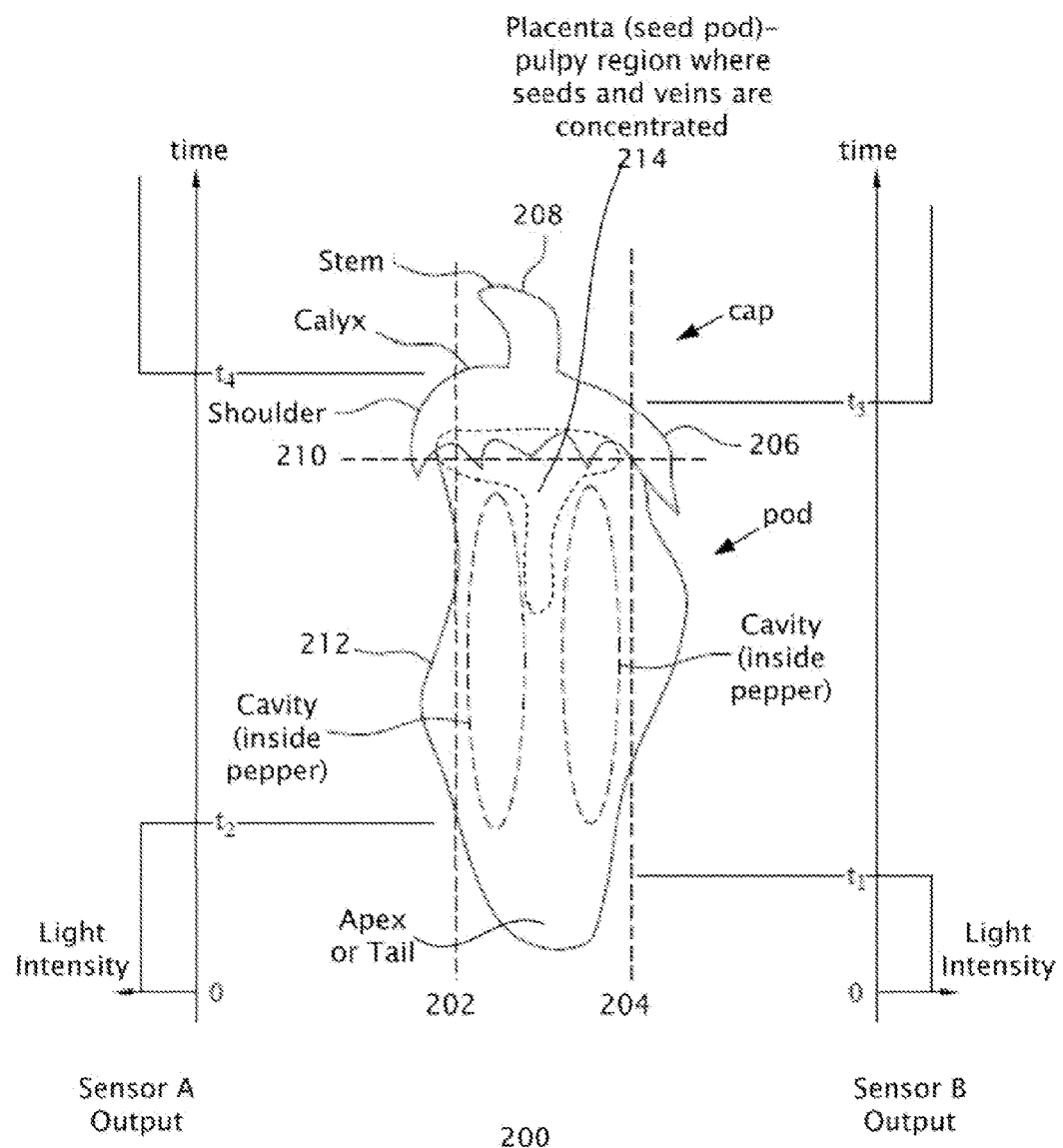
FIG. 2 shows a typical pepper to be de-stemmed.

FIG. 2 shows a typical whole pepper 200 to be de-stemmed. The typical terms used to describe a pepper 200 are indicated in this drawing. A typical whole pepper 200 includes a stem 208 and a calyx 206. The pepper also includes a placenta 214 that is typically a pulpy area including veins and seeds. In food processing, it is typically desired to separate the calyx 206 and stem 208 from the body of the pepper 212, typically at a line 210. In de-stemming a pepper, it is typically desired to place the cut 210 such that as much of the body of the pepper 212 as possible is retained for further processing into food products, and such that the cavity is not exposed to outside air.

A method of shoulder recognition takes advantage of the typical shape of a pepper to remove the stem by looking at exterior characteristics of the pepper. The method allows the cut 210 to be placed such that the stem 208 and calyx 206 are removed from a pepper typically resulting in a minimal waste of the body of the pepper 212.

To implement shoulder recognition, two or more sensors may be disposed beneath the path of a pepper 200 being processed in one example of a pepper de-stemming machine. In another example of a pepper de-stemming machine to be described, a vision system may be used to examine the exterior. In further alternative examples the interior of the pepper may be examined by passing a signal through the pepper and looking at a signal or image produced by the varying density of the pepper.

The pepper 200 generally passes by the sensors or cameras in the line of travel denoted by lines 202 and 204 when it is fed into the de-stemming machine. In looking at the exterior of the pepper at least two light sources supply light to the sensors to allow detection of the shape of the pepper. For example, light sources, such as lasers, may be disposed above the pepper 200 to shine into a sensor disposed beneath the pepper until the pepper blocks the light. For two sensors, sensor A and sensor B, their output may be as shown, as the pepper passes over the sensor. Before the pepper reaches either sensor, a light intensity is recorded by the sensors. As the pepper body covers the sensors, the light intensity is reduced or eliminated as shown at time t1 and time t2. As the pepper travels down the line, the light sensors are uncovered producing a light reading at the sensors generally indicated at time $t_3$ and $t_4$ time. Thus, by utilizing the shape of the pepper and examining its exterior, the shoulder of the pepper may be detected using the sensors. Once the shoulder of the pepper is detected, a signal is produced to cause removal of the stem and calyx from the pepper at line 210. Alternatively, mechanical switches, vision recognition systems, or a combination of vision and laser may be used to detect the pepper shoulder based visual characteristics of the pepper exterior.

I. De-Stemming Based on Evaluation of the Exterior

I. A. De-Stemmers

FIG. 3 is a flow chart of a method of de-stemming a pepper utilizing mechanical, or laser, shoulder recognition based on exterior examination. First, a pepper is provided to the input of a pepper de-stemming machine 301. Next, the pepper is oriented such that the apex end of the pepper is presented to the de-stemming machine first 302. Next, the pepper travels into the de-stemming machine such that a first sensor is blocked by the body of the pepper 303. At nearly the same time, a second sensor is blocked by the body of the pepper

304. As the pepper travels further into the de-stemming machine, either the first sensor or the second sensor is unblocked by the body of the pepper then the other 305. A reading is produced at the first sensor, and the second sensor that may then cause a knife mechanism to remove the pepper calyx once the pepper travels underneath an automated knife 306.

In the mechanical switch activated shoulder recognition example, and the laser and sensor combination examples used in shoulder recognition, the control systems may be manually adjusted to provide the proper timing for the de-stemming of the pepper. For example, motor speed governing the belt may be adjusted and the time between shoulder recognition and actuation of the knife blade may be adjusted by hand.

FIG. 4 is a flow chart of a method of de-stemming a pepper utilizing machine vision or a combination of machine vision and laser shoulder recognition that examines an image made of the pepper. In an example of a pepper de-stemmer utilizing machine vision, in addition to shoulder recognition, the machine vision pepper de-stemmer may detect the orientation of the pepper 401 in a chute, or on a belt, feeding the de-stemmer so that apex first or stem first orientation of the pepper in the cluster or on its belt may be detected. Examination of the pepper image utilizing conventional image processing may allow the shoulder to be detected 407.

Also, the vision system can allow for detection of the color 402 of the pepper for grading a separate purpose. Previously, color differentiation may have been handled by selective harvesting, or a color sorting machine. Now, color differentiation or sorting may be achieved while de-stemming on a single machine allowing for more efficient processing.

The vision system may also detect defects 403 in the pepper. For example, if the pepper being fed into the machine is not whole, or is broken, the de-stemming machine may detect this. In an alternative example, the machine vision pepper de-stemmer may also be capable of detecting blemished peppers by color recognition. And finally, machine vision may allow shape recognition to detect crooked peppers 404. The machine vision pepper de-stemmer also allows for size recognition 405 of the various types of peppers, for example, jalapeños peppers may be much smaller than the large varieties of chili peppers. And finally, a signal is generated to de-stem the pepper 406.

FIG. 5 is a schematic showing a pepper de-stemmer utilizing mechanical shoulder recognition 500. As previously described, mechanical switches 503, 504, 505 and 506 may be utilized to implement the method of shoulder recognition. As shown, a conveyor belt 501 causes an orientated and singulated pepper 502 to travel up to and contact a pair of mechanical switches 503, 504. Switches contact the pepper at the apex end and rise and fall over the body of the pepper as the shoulder of the pepper is approached. Once both switches 503, 504 begin to fall, a signal is sent to a knife assembly 509, 510 and 511 to cut the calyx off of the pepper when the pepper reaches the knife assembly.

To improve performance, a pair of switches may be used on the bottom of the pepper and on the top of the pepper as shown. Increasing the number of switches tends to improve the triggering of the knife assembly particularly for irregular shaped whole peppers. As shown, a relay 507 is tripped and after an exemplary delay of 0.02 seconds a 4-way air solenoid 508 is activated. An air ram 509 pushes a knife blade 511 down, de-stemming the pepper at the appropriate time. Depending upon the machinery used, and the parameters governing the machinery such as belts speed inclination and the like, the time interval between the activation of the knife and the detection of the shoulder may vary.

FIG. 6 is a schematic showing a pepper de-stemmer utilizing laser shoulder recognition 600. The laser vision system typically utilizes a pair of lasers 602 and corresponding receivers 602 to detect the light. A pepper may be lying on a belt 501 that is fed past the sensors 601 and lasers 602, or it may be fed through an inclined chute into belts. The pepper typically interrupts the laser beam as it passes by the sensors. The sensors may be disposed more or less parallel to each other at each side of the pepper's path. The pepper is typically oriented such that the pepper body interrupts the laser beam at the apex end first. First, the apex end of the pepper interrupts the laser beam on both sides at each receiver. Next, as the shoulder slopes away from the body of the pepper, the laser beam is unblocked causing the air ram 509 and knife 511 to be activated after an appropriate time. After interrupting the laser beams, the pepper travels past the air ram and knife assembly for de-stemming. A pair of amplifiers 603, 604 are typically utilized, one set to a one shot in the range of 25,000 at 0.025 snap. Amp 2 607 produces a 24 volt DC output causing a 4-way air relay to be activated. The output of the air relay 507 provides air to actuate the air ram 509 having a knife 511 disposed at the end of the air ram's piston. The air relay 507 is operated by conventionally supplied compressed air 512 and may include an exhaust.

FIG. 7 is a schematic showing a whole pepper de-stemmer utilizing machine vision shoulder recognition. A vision only whole pepper de-stemming system, include whole peppers disposed at various positions as they pass underneath the de-stemming machinery. A conveyor belt is provided so that the whole peppers lie on the belt and pass under the vision system. An encoder is coupled to the conveyor belt to tell the programmable logic controller ("PLC") how fast the conveyor belt is moving. As the pepper rests on the belt, and travels towards the pepper de-stemming machinery, lighting may be provided, such as by a fluorescent light or its equivalent, to illuminate the whole pepper so that a proper image may be made by the camera. A conventional optical sensor is provided to trigger the camera, causing an image of the whole pepper to be made which is sent to the PLC.

The PLC utilizes data encoding software to process the image made by the camera. The PLC is able to determine the orientation of the whole pepper, that is whether the apex or the stem end is traveling first into the de-stemmer. This eliminates the need to orient or singulate whole peppers prior to de-stemming. The PLC determines which end of the whole pepper is passing through first, and by recognizing the image of the whole pepper is able to adjust the signal provided to the knife to cut off the pepper's calyx. In addition, the time to cut off the stem is calculated by taking the encoder reading into consideration when sending signal to the air ram. As previously described, an air relay operates off of a 24 volt DC signal provided to it to supply air to the air ram actuating the knife.

In addition to recognizing which end of the whole pepper is present in timing the actuation of the knife, the vision system is able to examine the peppers and determine pepper color and quality by comparing known data points. The PLC issues a "don't cut" signal which is provided when discolored, crooked peppers or otherwise defective peppers are detected. A 24 volt DC signal from the don't cut line is provided to an air activated solenoid such that the rejected whole pepper passes through the de-stemmer uncut. Rejected peppers may be ejected to a conveyor belt carrying them to a rejects bin by a jet of air or other equivalent methods.

FIG. 8 is a schematic showing a whole pepper de-stemmer utilizing a combination of machine vision and laser shoulder recognition 800. A combination of a vision and laser system may also be similarly provided. A vision system 801 typically determines orientation of whole peppers and provides a pass or fail output for rejecting miss-shaped or discolored peppers. Once the pepper passes the vision system 801, a pair of laser heads 601, 602 coupled to amplifiers 603, 604 create a trip signal to activate the air ram 509 causing the cutter head 511 to clip the calyx and stem off the whole pepper. Otherwise the vision systems and laser systems operate as previously described.

I. B. Processing Assembly Incorporating the Third Example of a Pepper De-Stemmer (Machine Vision)

FIG. 9 shows a perspective view of an example of a whole pepper de-stemming machine or production system 902 utilizing machine vision for shoulder recognition and a belt system to feed whole peppers for de-stemming 901. Also shown are various feed 904 and removal systems to handle whole peppers 904, de-stemmed peppers 906 and debris 908. This figure shows an exemplary whole pepper de-stemmer having a conveyor belt feed 910 preceded by a vibrating conveyor 912 for vibrating whole peppers into lanes for processing. The machine processes multiple lanes of peppers simultaneously to increase capacity. The example includes 20 conveyor belts suitable for a modularized design of a whole pepper de-stemmer. The conveyor belts 904 carry the peppers to the vision system 902 that operates as previously described. In this example, the control electronics are disposed at the side of the prototype assembly in a cabinet, or other convenient location. Such an assembly 901 when sufficiently modularized may allow improved maintenance. The entire de-stemmer apparatus 901 may also be constructed in modules, for incorporation in larger production lines for whole pepper processing and for flexible configurations to suit production needs.

FIG. 10 shows a side view of the example of the whole pepper de-stemming machine 901 utilizing machine vision shoulder recognition and a belt system to feed whole peppers into the de-stemmer from a vibration table 912. This view shows a side view of the whole pepper de-stemmer with the horizontal belts (not visible) in the de-stemmer 902 to carry multiple lanes of the longitudinally aligned peppers (either tail first or stem first) into the de-stemmer machine 902. Although a vibratory table 912 is shown to align the peppers, other equivalent devices may be used to get the peppers from a randomly oriented state into a longitudinal alignment.

I. C. Processing Assembly Incorporating the Second Example of a Pepper De-Stemmer (Laser)

FIG. 11 shows a perspective view of an early example of a single lane whole pepper de-stemming machine utilizing laser shoulder recognition and a single lane system to feed whole peppers for de-stemming. Whole peppers are singularized by placing them in the hopper 1102 with apex first orientation. Whole peppers pass through the hopper and drop through a tube where they are ejected 501 on a belt assembly 1104. At the end of the belt assembly, are the laser sensors and the laser sources 601, 602. The whole pepper interrupts the laser beam utilizing the herein disclosed method of shoulder recognition to activate the air ram 509 that chops the calyx and stem off of the whole pepper. Gravity causes the pepper to fall from the bottom of the air ram assembly. Control electronics are provided by modular assemblies on the side of the unit 1106. Air and AC power are external inputs supplied to the de-stemmer.

In this example, a series of drive belts 1104 are used to guide the whole pepper into the de-stemming machinery. Drive belts may be V-belts or any equivalent type of belt. Two belts at this side of the whole pepper are used to guide the whole pepper into the de-stemmer, with two belts being disposed at the bottom of the whole pepper to carry it through. All the belts typically run at the same, or nearly the same, operating speed.

In feeding whole peppers through the de-stemming machine, gravity feed may be utilized so that the whole peppers drop through the de-stemmer. In an alternative example, the whole peppers are fed horizontally or substantially horizontally on a conveyor belt.

At the shoulder end of the whole pepper, a pair of sensors beneath the whole pepper may detect light shining on both sides of the whole pepper, at two data points. While, at the apex end of the whole pepper that curls, the same two sensors would only detect one light data point as the whole pepper passes over the sensor. The curling end of the whole pepper would obscure one sensor from receiving light while the other side of the sensor would detect light. In the exemplary configuration, four data points or sensors are provided to detect the shoulder of the whole pepper with two sensors typically needed to recognize the shoulder.

After the lined up whole peppers are fed into the whole pepper de-stemming machine, the sensors help determine where the shoulder of the whole pepper is located. A time delay is built in such that once the whole pepper shoulder is recognized, the whole pepper travels to a knife assembly or an equivalent cutting device in a pre-calculated amount of time where the calyx and stem are chopped, or cut off.

In a typical example, the knife assembly is pneumatically extended and pneumatically retracted. The knife blade itself may be in a chisel type configuration for chopping or cutting off the calyx. In an alternative example, dual knives may be used. Since the whole pepper falls through the assembly and the single knife blade contacts the whole pepper, it tends to slip causing inaccuracy in the de-stemming procedure. The dual knife approach may improve the accuracy of the cut.

In another alternative example, a mechanism to hold the whole pepper in place while it is being cut may be provided. The mechanism to hold the whole pepper in place could be a spring loaded hold down, a boot, (such as a rubber boot), or a forked assembly to hold the whole pepper in place while it is being de-stemmed.

FIG. 12 shows a side view of an example of a whole pepper de-stemming machine utilizing laser shoulder recognition and an inclined quadruple belt system to feed whole peppers for de-stemming shown in FIG. 11. This figure shows a close up of the air ram assembly 509 and the laser sources 602 coupled to it. The piston assembly 1204 from the ram 509 is disposed on a bracket 1202 that supports the knife 511. The belt assembly 501 carries the whole pepper past the sensors (not shown) and sources 602 to cause an interruption in the laser beam. The control electronics process the sensor inputs in order to activate the knife blade 511 at the proper time. The machine as described above may be formed into modular assemblies suitable for assembly into a production line.

II. Assembly of Modular De-Stemmers and Processing Plant Layout

FIG. 13 shows an assembly of modularized whole pepper de-stemming machines 1301, 1302 into a production line for flexibility in production capacity and maintenance. A whole pepper de-stemming machine may be built and configured such that an exemplary multiple production lines of whole pepper de-stemming may be provided in those machines. Then multiple machines 1301, 1302 each having an exemplary 20 lines of processing may be coupled together. Modularity allows the repair of broken machines without shutting down a whole line, and also allows production facilities to tailor the processing to the size of their operation.

By modularizing or componentizing the whole pepper de-stemming apparatuses, flexible production lines may be established. Any number of whole pepper de-stemming modules that may be built as previously described may be coupled together to accommodate large volume of whole peppers or implement a desired production rate. The whole pepper de-stemming modules operate somewhat independently and may be coupled together, or placed in any convenient location to facilitate the processing of whole peppers. The modules themselves may be serviced easily since they are modular, and the components on each whole pepper de-stemming module may be further modularized for ease at replacement and servicing. Thus, if one whole pepper de-stemming module were to malfunction, it may be replaced until satisfactory service can take care of it without substantially slowing the flow of production.

FIG. 14 shows an example of a whole pepper de-stemmer 1401 that may be built as previously described working in conjunction with additional components for processing whole peppers such as singularity processing, grading and the like. By utilizing modular construction, the whole pepper de-stemming module 1401 may be coupled to other components 1402 and 1404.

As shown, whole peppers 1403 are fed to an optional feed or singularity processing modules 1402 where they are in turn fed via a transport mechanism 1408, into a whole pepper de-stemming module 1401, after being de-stemmed, the whole peppers may pass through one or more integral processing modules, such as 1404 where stems and calyxes may be ejected 1405 and defective whole peppers 1407, or de-stemmed whole peppers 1406 may be outputted. An additional processing module 1404 may be utilized to further process the de-stemmed whole peppers. Defective whole peppers may include those that are blemished, discolored or have undesirable shapes.

In addition to, conventional methods of selective harvesting practiced in the field, color sorting 1407 at the warehouse or other location may be performed utilizing the vision version (shown in FIG. 8) of the whole pepper de-stemming machine 1401. Color sorting at the warehouse using a conventional color sorter has a typical efficiency of 80%. With the machine vision version of the whole pepper de-stemmer, a typical color sorting efficiency is approximately 100%.

By utilizing an automatic pepper de-stemmer as described above, manual labor may be reduced and the production output of de-stemmed whole peppers may be increased. A typical processing speed for a pepper de-stemming machine is approximately 2.5 whole peppers per second, per line. Thus, an approximate output of a 20 line whole pepper de-stemming operation would be approximately 50 whole peppers per second.

In processing the whole peppers, a singularity process 1402 is typically first utilized to put the whole peppers in line before de-stemming. Singularity may be accomplished by placing the whole peppers in line by hand or by mechanical means such as aided by a vibration table or equivalent, so that the calyxes are all at the same orientation entering the de-stemming machine so that the whole peppers may be placed in line having mixed orientation of stem to apex. The mixed stem to apex orientation of whole peppers may be utilized in the machine vision whole pepper de-stemmer. An orientation having the stem and calyx in the same position would be utilized in a mechanical switch version, or a laser version of the whole pepper de-stemmer. Once oriented properly, the whole peppers are fed to a sensing mechanism.

The whole peppers may be transported 1408 through a belt system from a tube hopper or other suitable input device. In an example of the pepper de-stemmer, 4 v-belts are configured such that the pepper rests on 2 v-belts and the remaining 2 v-belts travel along the side of the pepper providing enough friction to push it into or through the whole pepper de-stemmer mechanism.

In the machine vision version (shown in FIG. 8) of the whole pepper de-stemmer utilized in the embodiment of a de-stemmer 1401, a micro processor is utilized to control the vision component of the whole pepper de-stemmer. The processor typically includes software which accepts the sensor data as inputs processes the inputs and then provides control outputs for detecting the orientation of the whole pepper, determining the color of the whole pepper, determining if the whole pepper is defective and shoulder recognition. The micro processor also provides control signals carrying out for disposal of defective whole peppers, and the calyx, as well as sorting from the primary receptacle or bin, to an auxiliary receptacle or bin for whole peppers not meeting the color criteria desired. The pepper de-stemmer may be coupled to other processing machinery 1404.

An example of an integral processing module 1404 may be a pepper boat maker. A pepper boat maker is further described in U.S. patent application Ser. No. 12/104,343, filed Apr. 16, 2008, the contents of which are incorporated herein by reference. in utilizing a boat maker processing module 1404 the pepper is first de-stemmed by the de-stemming module 1401, and then enters the processing module 1404, where the boat maker apparatus splits the pepper longitudinally, and removes seeds and veins to form two longitudinally de-stemmed, de-veined, and de-seeded pepper boats.

FIG. 15 shows a floor plan for a pepper processing facility utilizing pepper de-stemming machinery. In this example of a processing facility peppers brought in from the field in a trailer 1502. The peppers were unloaded via an inclined belt 1504, into sizing equipment 1506. The sizing equipment 1506 separates the peppers into bins containing small medium and large peppers. The peppers may also be sorted into a bin of peppers for use in making pepper boats. The bins 1508 are then taken to the pepper to stemming machine set up 1528. Here the bins 1530 are dumped into a hopper with a metered feed 1530. The peppers fall onto an inclined feed 1510 where the next fall onto a vibratory alignment conveyor 1512, two line them up before they entered the de-stemmer machinery 1514. Peppers processed by the de-stemmer machine 1514, may be sorted onto a conveyor 1516. Sorting may be provided to remove peppers having an undesirable color from acceptable peppers to be de-stemmed. The stems may be removed for 1520, and taken away by a conveyor 1518. The de-stemmed peppers may pass over a visual inspection table 1522, and up an incline conveyor 1524, where they fall into a bin 1526.

FIG. 16 is a flow diagram showing pepper processing in a facility utilizing pepper de-stemming machinery. Processing of peppers from the field to shipping is described in this process flow diagram. At 1602 peppers are harvested and loaded into field trailers. At 1604 peppers are transferred from the field trailers into a large, typically 40,000 pound trailers for transport to a processing facility. At the facility of peppers may be quickly unloaded from the trailer for trash removal and bulk storage 1606. Large trash removal may be accomplished by air to dispose of stems and leaves 1608. The cleaned peppers may be conveyed into another exemplary 40,000 pound trailer where they may typically be transferred to 1,500 pound plastic bins 6012, for later transfer to 8,000 pound bulk hoppers with leaders the 1614. Alternatively, the peppers at 1610 may be transferred directly to 8,000 pound bulk hoppers 1614.

Peppers placed in the 8,000 pound bulk hopper with metered feed 1614, are then run through an exemplary Kerian sizer to sort peppers from remaining trash and to size peppers typically into small, medium, or large sizes. These exemplary size gradings provided are not limiting. It is worth relating that better results from the de-stemmer are obtained when variations in size among the peppers presented to it are reduced. Uniform size in a batch of peppers presented to the de-stemmer tends to allow a more accurate cut to be provided. At 1620 the size peppers are distributed into bins according to their size. The peppers maybe taken to cold storage 1622 and then, at a later time taken to an exemplary 2000 pound hopper 1624. Alternatively the peppers separated into the bins at 1620 may be directly dumped into the 2,000 pound hopper 1624. After block 1626 an inspection conveyor may be provided.

A cleated incline feed the 1628 raises the whole peppers to input them to a vibratory laneing conveyor 1630. The whole peppers then enter the de-stemmer 1632, were mis-colored peppers may be disposed of via a trash conveyor 1634. The peppers of acceptable color are de-stemmed and fall onto to a conveyor along with the removed stems 1636. After block 1638 stems may be removed by machine or by utilizing rollers. At block 1640 visual inspection and hand removal of defective de-stemmed peppers may be done, with the defective peppers being placed in a defect bin 1642. The good peppers exiting from block 1640 interim incline which may include a magnetic slide for metal removal 1644. From there the good de-stemmed peppers may be put into an exemplary 36 inch (or its equivalent) fiber or plastic bins for protocol, cold storage, and shipping.

III. General Processor Description

FIG. 17 is a block diagram of a general purpose computer system 1700 capable of providing control signals for implementing a method of de-stemming a pepper as described herein. Such a system may be disposed in a cabinet coupled to the de-stemmer machine, or disposed nearby, such as against a wall or in another convenient and out of the way location. Exemplary computing environment 1700 is only one example of a computing system, and is not intended to limit the examples described in this application to this particular computing environment. Computing environment 1700 is simply the most general of numerous computing environments in which the methods described herein may be implemented to control de-stemming. Other examples of controllers include conventional programmable logic controllers and their equivalent.

For example the computing environment 1700 can be implemented with numerous other general purpose or special purpose computing system configurations. Examples of well known computing systems, may include, but are not limited to, Keyence Vision System, and Keyence Programmable Logic Controllers, microcontrollers, microprocessors, laboratory controllers, instrument controllers, process controllers, personal computers, hand-held or laptop devices, microprocessor-based systems, multiprocessor systems, and the like.

In addition one or more processors may be employed. For example a microprocessor or a system of microprocessors can be configured to control a single de-stemmer lane independently, or they may be coupled to a controller computer to coordinate the operation of other de-stemmers, and/or other machinery in the processing flow, such as shown in FIGS. 13-16. Alternatively each de-stemmer lane may run completely independently of any other device. And alternatively, a single general purpose computer can be configured to control processing of all lanes.

The computer 1700 includes a general-purpose computing system in the form of a computing device 1701. The components of computing device 1701 can include one or more processors (including CPUs, GPUs, microprocessors and the like) 1707, a system memory 1709, and a system bus 1708 that couples the various system components. Processor 1707 processes various computer executable instructions, including those to provide shoulder recognition and other de-stemmer control signals 1724 and to control the operation of computing device 1701 and to communicate with other electronic and computing devices (not shown) via an I/O interface 1722, if needed. The system bus 1708 represents any number of several types of bus structures, including a memory bus or memory controller, a peripheral bus, an accelerated graphics port, and a processor or local bus using any of a variety of bus architectures.

The system memory 1709 includes computer-readable media in the form of volatile memory, such as random access memory (RAM), and/or non-volatile memory, such as read only memory (ROM). Typically program instructions such as the pepper de-stemming method 710 are resident here, for ready execution after being uploaded from the hard disk 1710. A basic input/output system (BIOS) is stored in ROM. RAM typically contains data and/or program modules that are immediately accessible to and/or presently operated on by one or more of the processors 1707.

Mass storage devices 1704 may be coupled to the computing device x01 or incorporated into the computing device by coupling to the buss. Such mass storage devices 1704 may include a magnetic disk drive which reads from and writes to a removable, non volatile magnetic disk (e.g., a "floppy disk") 1705, or an optical disk drive that reads from and/or writes to a removable, non-volatile optical disk such as a CD ROM or the like 1706. Computer readable media 1705, 1706 typically embody computer readable instructions, for pepper de-stemming data structures, program modules and the like supplied on floppy disks, CDs, portable memory sticks and the like.

Any number of program modules including methods for de-stemming peppers 710 can be stored on the hard disk 1710, mass storage device 1704, ROM and/or RAM, including by way of example, an operating system, one or more application programs, other program modules, and program data. Each of such operating system, application programs, other program modules and program data (or some combination thereof) may include an embodiment of the systems and methods described herein.

An optional display device 1702 can be connected to the system bus 1708 via an interface, such as a video adapter 1711. A user can interface with computing device 1701 via any number of different input devices 1703 such as a keyboard, pointing device, joystick, game pad, serial port, and/or the like. These and other input devices are connected to the processors 1707 via input/output interfaces 1712 that are coupled to the system bus 1708, but may be connected by other interface and bus structures, such as a parallel port, game port, and/or a universal serial bus (USB).

Computing device 1700 can operate in a networked environment using connections to one or more remote computers through one or more local area networks (LANs), wide area networks (WANs) and the like. The computing device 1701 is connected to a network 1714 via a network adapter 1713 or alternatively by a modem, DSL, ISDN interface or the like.

IV. Cutting Assembly with Hold Down

FIG. 18 shows a cutting assembly 1800 with a hold down 1802 to keep the pepper 1804 from moving, or shifting when cut. The assembly attaches to the air ram piston 1806. As the cutting assembly travels down, the pepper is held down by a spring loaded hold down or pod 1808, before the blade 1810 cuts the pepper 1804.

V. Further Detail of the Third Example of a Pepper De-Stemmer (Machine Vision)

FIG. 19 shows an exterior vision system for implementing a method of shoulder recognition in one lane of a pepper de-stemmer. This system may be included in other types of pepper de-stemming systems as well as being used on it own. As shown, a pepper having a blossom end 1902 and a stem end 1904, travels so that it is positioned underneath a camera 1906 as it moves down the production line. The camera 1906 is conventionally constructed and may work in conjunction with a conventionally constructed illumination source (not shown). The camera 1906 sends a conventional video signal 1908 to a conventionally constructed image processing system 1910 that may include one or more conventionally constructed microprocessors 1912.

In the example shown, a Keyence vision processing system providing area continuance image processing, as produced by the Keyence Corporation may be utilized for the image processing system 1910. Area continuous measurement simply refers to the continuous measurement of an area in an image window looking for specific color information. Equivalently, other methods of monitoring a desired area for a specific color may be utilized including the capture and analysis of a plurality of discrete frames. The exemplary vision system may also be configured to provide a plurality of user defined image windows for internal analysis of an image. Windows allow certain pixel information to be extracted from a given area. Equivalently, windows having differing shapes may be provided, including round, oval and the like. In the example shown, six rectangular windows have been preconfigured to provide six output signals 1914 from the Keyence or other vision processing system. The six signals from the Keyence vision processing systems are conventionally formatted by conventional image processing methods. Information from the windows can be used to set triggers, set minimums, set maximums, to implement pixel counts and the like in a subsequent instrumentation control module 1916. The output from the image processing module 1919 is coupled to a PLC 1916 that executes, an embodiment of the method of pepper de-stemming that uses information from the vision processing system 1910 to control pepper de-stemming machinery 1918, 1920 as determined by the PLC 1916. The PLC 1916 may include one or more microprocessors, memories and the like 1922, for implementing the method of pepper de-stemming.

By processing information supplied from the strategically placed windows, the method of pepper de-stemming utilizes this information to provide output signals to an air ram coupled to a knife blade 1920. The output signals may include a "stem first" signal 1924 and "tail first" signal 1926 which may be coupled together to actuate the air ram 1918 at the appropriate time to de-stem the pepper. The method of pepper de-stemming also analyzes video signals from the vision system 1910 to produce an actuation signal to an air port (or blow off port) 1928 to reject discolored or otherwise undesirable peppers.

FIG. 20 shows an end view of a pepper resting on drive belts used to transport it along a production line during processing. This particular configuration can aid the camera 1906 in recognizing the pepper 2002 shape. The pepper 2002 rides above the work area on the belts 2004, 2006. The drive belts are conventionally constructed and are selected such that a pepper 2002 being transported by the drive belts 2004, 2006 typically does not contact an image background area 2008 that is the same color as the drive belts 2004, 2006 and disposed beneath the belts. By supporting the pepper above the imaging area, rubbing that may cause discoloration of the image background 2008 can be prevented. In addition, an additional belt cleaning mechanism (not shown) may be provided to continuously clean the belts maintaining their color for the image processing. Also, additional cleaning equipment may be provided to clean the work area during use to prevent discoloration and accumulations of dirt and organic waste. For example, the work area may be the surface of a belt so that the work area rotates through a cleaning mechanism. Or, the work area may be in the path of an air jet to blow off dirt and debris that may tend to collect is the image area.

The belts and the work surface in the example shown may be of the same color. The color chosen in this example is a florescent orange, and the particular model of belt in this example is made by Fenner Drive of Leeds UK, Eagle Polyurethane Belting Division and is a 3LT model in Eagle Orange 85. The exemplary 3LT model belt is conventionally constructed to a T top belt which tends to work well in the given application of pepper de-stemming. However, other equivalent belt configurations and colors may be substituted satisfactorily.

In particular, other colors may be found to work better in other applications processing different colored products. Typically, it may be best to select a belt and work surface that does not contain colors of the thing being processed. In general, florescent colors tend to work well since they tend to reflect their own color. It has also been found that in de-stemming green peppers that red, black, white and green belts tend not to work very well. However, pink, blue, yellow and the already mentioned orange colors may provide satisfactory performance. In general, any color belt or background materials that are of a color not found in the object being imaged, tend to enhance the vision recognition process used in determining shoulder location to de-stem the pepper.

FIG. 21 shows an overhead view of a pepper traveling along a production line that will be de-stemmed using the method of shoulder recognition that uses the vision system of FIG. 19. Shown here are exemplary windows that may be defined to aid in the method of shoulder recognition. As the pepper 2002 travels into an imaging area 2102 on the belts 2004, 2006, the camera positioned above (not shown) captures an image of the pepper that may be displayed on a monitor 2104. The monitor may also include user configurable image processing windows 2106. Image processing windows (1, 2, 3 & 4), may be sized and placed as needed to implement de-stemming. Placement may be dependent upon the crop, and type of peppers being de-stemmed. In the example shown, four windows are shown 2106. The four windows shown are selected to allow determination of the orientation of a pepper as it is passing along the production line, towards the knife 2108 that will de-stem it. The windows 2106 are typically centered along an axis formed by the peppers direction of travel 2110. The first and fourth windows are typically larger than the second and third windows. And, the fourth window is typically longer (as measured along the direction of travel) than the first window to facilitate de-stemming.

The image area 2102 is typically configured so that it covers the imaging background 2008, the belts 2004, 2006 and the pepper 2002 passing along the production line. The imaging area 2102 and the belt width may be set up so that an image of the entire pepper may be captured, or only a portion of the pepper's image is captured as it travels over or through the imaging area, which ever is found to work best for a given crop, or pepper type.

The windows 2106 when used in conjunction with specifically configured processing method in the PIC (1916 of FIG. 19) allow determination of the location of the peppers shoulder so the stem can be removed. When the pepper travels a distance "d" to the knife blade 2108, actuation of the knife blade may be timed so that stem is removed from the pepper 2002 at the shoulder line 2111. Prior to the knife blade 2108 being actuated, a hold down 2112 may be provided that tends to hold the pepper so it does not tip up, or otherwise move out of position while being de-stemmed.

An air jet 2114 may also be provided so that discolored or otherwise undesirable peppers may be ejected from the production line with a stream of air. In finding discolored peppers, the imaging windows may also be used to determine if a pepper is discolored or otherwise undesirable. The air jet causes undesired peppers to be separated from the main section batch by blowing them off of the line. Alternately, other methods of removing peppers may be employed. Once the implemented method of de-stemming a pepper determines that a pepper is to be rejected, it generates a signal to open an air jet so that the pepper is blown away from the production line to a discard area, or bin when it reaches the air jet.

FIG. 22 is a process flow diagram showing a sequence of steps and logic to aid in programming a typical logic control module to run a de-stemmer machine such as the exemplary control module (1916 of FIG. 19) at a register level. Logic #1-4 refers to the inputs received from the previously set up windows configured to output a logic signal responsive to a pixels collected in a window. Also included are various truth tables to aid in control circuit programming of the exemplary PLC control module, such as one made by Keyence or its equivalent.

FIG. 23 is a generalized process flow diagram of the de-stemmer example shown in FIG. 19. At block 2302 the first color sensor is set. Here the trigger is set to an exemplary value of 250. At block 2304 the second color sensor is set to trigger at an exemplary value of 1000. At block 2306 peppers are fed into the de-stemmer machine. At block 2308 in inquiry is made to determine if the first color was triggered first. If the first color was triggered first control passes to block 2320. If the first color was not triggered first control passes to block 2310.

At block 2320 is determined that the pepper is in stem first. At block 2340 the second color sensor is read. At block 2342 if it is determined that the "dark on" value has been achieved then the stem first pepper is de-stemmed at block 2344.

At block 2310 it is determined that the pepper is tail first. At block 2312 it is determined the color 2 has triggered. Next at block 2314 color 2 "dark on" is triggered. At block 2316 color 2 "light on" is triggered. And finally at block 2318 the tail first pepper is de-stemmed.

VI. De-Stemming Based on Evaluation of the Interior

VI. A. Processing Assembly with Infrared De-Stemmer

FIG. 24 is a diagram of processing machinery that inputs harvested peppers and produces peppers that are de-stemmed by a de-stemmer machine included in the processing machinery. In this example of pepper processing machinery a pepper de-stemmer utilizing infrared sensors is used to look through the pepper. By utilizing the increased density present in the stem, and the placenta the process determines where to make the cut to de-stem the pepper based on the level of a signal that passes through a pepper. In all of the following examples IR sensors employing a transmitter and receiver pair are utilized. However in equivalent examples other types of sensors such as RF, microwave, magnetic resonance and the like may be equivalently substituted for the IR sensors with the appropriate adjustments made by one skilled in the art to account for differing sensors differing characteristics.

First bulk whole peppers are loaded into a hopper 2402. From the hopper the peppers fall onto a hopper conveyor 2404. From there the peppers travel up an incline conveyor 2406 and fall into a vibrator hopper 2408. The peppers are distributed onto a vibrating table (or vibrator) 2410 and are then distributed onto multiple lanes of the de-stemmer 2420. The de-stemmer picks peppers up with v-belts 2412 and carries the peppers over infrared emitters (or equivalently infrared transmitter) mounted beneath the lane and infra red receivers disposed opposite the emitter, and positioned between the v-belts 2414. An actuator knife 2416 de-stems the peppers based upon information determined from the infrared sensors 2414. The de-stemmed peppers, and the stems, fall onto a take away conveyor 2418 and are carried away for further processing. The electronics (not shown) containing the processor that actuates the knife 2416 based on signals from the infrared sensors 20 414. The electronics may be placed at any convenient position including attaching it to the de-stemmer 2420 or placing it in any other convenient location.

FIG. 25 is a schematic diagram of the de-stemmer machine of FIG. 24, with the electrical connections shown of a representative single processing lane 2502. Also included in the diagram is the wiring for motors and motor controllers 2504, the wiring for a belt tightening solenoid 2510 (in this example a belt tightening and relaxing apparatus is provided to release belt tension when the machine is not in service to improve belt life by reducing belt stretch.), wiring to the air's supply solenoid to control the knife assembly 2512 and other connections.

The wiring for the first lane 2502 is repeated for each lane present in the de-stemming machinery, and need not be repeated in this diagram. In particular this example includes a programmable logic controller Keyence model PLC KV-16DT that is program with a method of de-stemming 2506. Other equivalent controllers may be substituted for the one shown. Equivalent controllers include those of the type shown that are programmed by manipulating registers, timers, and the like to provide control signals at various times. Equivalently a PC can be provided that implements the method directly by generating a set of control bits as outputs based on inputs received from the sensors. The PLC KV-16 DT receives inputs from a three sensors and provides an output to the knife control circuit 2508. In this particular example the knife is powered by an air valve with a control signal applied to a solenoid releasing the air and causing the knife to de-stem the pepper. The knife is bi-directional and de-stems peppers with a forward stroke and a back stroke.

FIG. 26 is a process flow diagram showing a generalized method for de-stemming peppers utilized in the example of FIG. 24. This is the method of de-stemming peppers that is directed by programming of the Keyence PLC KV-16DT of FIG. 25. First motor control is provided to convey the pepper (or equivalently "product") to the de-stemmer 2602. The product being conveyed to the de-stemmer is oriented lengthwise, with either the stem or the tail entering the de-stemmer first. The stem end is detected with either optical or mechanical sensors 2606. The product is tracked to the cutting device with various timers being applied based upon whether or not the stem or tail is entering first. At the allotted time the stem end of the product is removed 2610.

In detecting the stem end, sensors are examined for signals that are indicative of the density and width of the stem, which tends to be distinct from the density and profile (the stem is much narrower) of other parts of the pepper. The sensors also are utilized to detect the density of placenta as the seeds in the veins that converge in that area produce a unique density profile as the density tends to increase as the stem end is approached. If a density characteristic of the stem is detected before a characteristic density of the placenta then the pepper is stem first, and vise versa. This is because the placenta tends to fill the calyx and shoulder area of the pepper, which is the area where a cut line (210 of FIG. 2) it is most advantageously placed. Thus, by examining the density of the pepper it can be determined if the stem or tail is entering the de-stemmer first, and by further examining the density it can be determined where to place the cut on a given pepper.

Different numbers of sensors can be equivalently used to implement this method. For example one sensor may be utilized to scan the pepper for density characteristic of the stem. Then one or more other sensors may be used to scan the pepper for density characteristic of the placenta. Additional sensors may be used that are optimized for peppers of varying sizes. In addition the sensors may be configured with receivers and emitters having various sensitivities and power outputs depending on the equipment available and the type of product being de-stemmed. Thus a variety of types of sensors, and a variety in the number of sensors may equivalently be utilized to implement the above described methods.

FIG. 27 is a process flow diagram showing details of an example of a generalized method for de-stemming peppers that employs two infrared sensors of FIG. 24. This diagram shows the further detail of the diagram of FIG. 26 that would aid one skilled in the art in programming a logic controller such as the exemplary PLC KV-16DT. In equivalent examples programming or logic based on FIG. 26 may be also be produced to aid in programming the specific device at hand.

The program monitors a first sensor that has been set to detect stem/seed placenta density. When the correct density has been detected an input provided by the sensor turns on. Next a one shot timer bit is set. For this controller this condition a shown by internal bit 3000 turning on for one scan.

When internal bit 3000 is on, the program next checks to see if the second sensor is clear. If the second sensor is clear then internal bit 1000 is turned on for one scan. In this example internal bit 1000 is used to indicate that the stem is coming first as the pepper enters the de-stemmer. In this example the "not cutting timer" is applied to keep the knife from cutting the same pepper twice.

If bit 1000 is on, then a hold in bit 1002 is set and a stem first delay timer T000 is started. Bit 1000 is only on for one scan, so bit 1002 holds in the timer T000 until it times out. Timer T000 is adjusted to allow the pepper to travel to the knife, and since the pepper is stem first, the time is set a little longer to get the knife edge past the cap of the pepper.

If bit 1001 is on, then a hold in bit 1003 is set and a stem first delay timer, T001 is started. Bit 1001 is only on for one scan, so bit 1003 holds in the timer T001, until it times out. Timer T001 is adjusted to allow the pepper to travel to the knife and since the pepper is stem last going into the de-stemmer, the time is set a little shorter to get the knife edge to cut the pepper before the cap.

Only one of the two timers T000 or T001 will be activated per pepper entering the de-stemmer because of the action of the one shots. But either of the two timers timing out, will triggered the internal bit 4000 one shot timer, where bit 4000 is the knife toggle one shot timer.

When bit 4000 is on, and the knife is already in the energized position, then the knife de-energizes. In this example the knife has two edges and swings from side to side so that it can cut one pepper on the forward stroke and another pepper on the backstroke. Alternatively when bit 4000 is on in the knife is already in the de-energized position, the knife then energizes cutting the pepper with the other edge of the blade.

When bit 4000 has triggered the knife in either direction, timer T002 is then reset to disallow second cut on the same pepper. Timer T002 is adjusted to a minimum distance between peppers that has been determined. When the tea 00 to timer has timed out that it allows the stem detect one shots to be set.

VI. B. Processing Assembly with Infrared De-Stemmer

FIG. 28 is a diagram processing machinery 2800 including an example of a pepper de-stemming machine 2802 that utilizes side mounted infrared sensors mounted in the sides of each pepper lane (the previous example utilized infrared sensors mounted below each pepper lane), and a bounce sorter to separate the stems from the de-stemmed peppers. This exemplary de-stemmer 2800 also includes a bounce sorter 2816 to separate the stems from the de-stemmed peppers. Thus, this pepper processing system 2800 inputs whole peppers 2820 and produces an output of de-stemmed or capped peppers 2822 separated from an output of stems and caps 2824.

Process flow proceeds in the direction shown 2818. First peppers are loaded into a conventionally constructed bulk loader 2812 and then travel up a conventionally constructed inclined ramp to a conventionally constructed pepper alignment and feed device to a pepper alignment and feed device 2810, where they fall onto a conventional vibratory table and are then input into the de-Stemmer 2802. Also included is a PLC cabinet 2804 that is part the de-Stemmer machine 2802. However the PLC cabinet could be mounted in any convenient location. An electrical control panel 2806 is also provided for the pepper processing system 2800 and may also be mounted in any convenient location. After the peppers leave the de-stemmer machine 2802 by a conventional conveyor belt, they enter a bounce sort machine to 816.

De-stemmed peppers leaving the bounce sort machine 2816 fall onto a de-stemmed pepper conveyor 2808 where they are transported for further processing or storage. The stems leaving the bounce sort machine 2816 fall onto a waste removal conveyor 2814 where they are moved away for disposal.

FIG. 29 is a diagram of a de-stemmer machine utilized in the processing system of FIG. 28. Here further detail is shown if the de-stemmer 2802 and the bounce sort machine 2816 shown in FIG. 28. Adjacent to the de-stemmer 2802 is a waste removal conveyor 2914 which has parallel to it a de-stemmed pepper conveyor 2908. Peppers leaving the de-stemmer 2802 travel a shorts distance where the bounce sort machine 2816 separates the stems from the de-stemmed peppers and deposits them on the waste removal conveyor 2914 and deposits the de-stemmed peppers on conveyor 2908.

FIG. 30 is a diagram showing peppers being carried through an example of a de-Stemmer machine (2802 of FIG. 28). Pneumatic actuators 3006 are mounted above the de-stemming lanes and each actuator is coupled to, and drives the knife having two edges the cuts the pepper on a forward or back stroke. Each actuator has two air (or gas) inputs and one electrical input. When a cut signal is applied to an actuator the knife is initially resting in a horizontal position either to the right, or to the left. When triggered, the knife swings down to make the cut then up to a resting horizontal position, opposite of where it previously was. Each knife is double-edged, and is positioned to overlap with a knife in an adjacent lane, without interfering, so the processing lanes can be spaced closer together. The actuators typically have two air inputs. One the air input drives the knife one direction, and the other air input drives the knife back to its previous position. This allows the knife to move back and forth. Cycling the double edged knife in this manner allows processing speed to be increased.

IR RX/TX sensor array 3010 is mounted in the side walls of each lane to keep dirt and debris from accumulating on the sensors, and so the sensors are out of the way of the belts conveying the peppers 3008. Multiple pairs of receiver sensor ("RX") and transmitter sensors ("TX") may be used, with the mating sensor disposed in the lane wall opposite its mate so that the pepper passes between the sensor pair interfering with the signal received in the mating RX sensor. Depending upon the TX sensor characteristics, the signal it emits may be blocked by the pepper, or attenuated by the pepper, depending on the characteristics of the signal transmitted. As the pepper in lane 3002 passes the IR RX/TX sensor array 3010, a signal is generated to appropriately actuate the knife 3004 so that the pepper is properly de-stemmed when the shoulder passes under the knife 3004. The de-stemmed pepper 3005 then falls from the de-stemmer.

FIG. 31 shows an example of a de-stemmer machine sensor array disposed in the side walls of a de-Stemmer lane (vertical sensor disposition) used in the processor example (2802 of FIG. 28). However in alternative examples one or more sensors or detectors may be disposed beneath the lane, particularly when infra red sensors may be used to illuminate and otherwise examine the interior density of a pepper to be de-stemmed. The front view of the IR RX/TX sensor array 3112 shows two sensor arrays 3114, 3116 mounted in the walls of a pepper de-stemming lane. The sensors shown may be receiving or transmitting modules or a mixture thereof. The opposite wall of the lane 3120 includes receiving or transmitting sensors mated to the corresponding sensor. One of the sensor arrays 3116 is positioned lower than the other sensor array 3114. Both sensor arrays function in the same manner. However, the first sensor array 3114 is higher so the large peppers may be scanned effectively, and the second sensor array 3116 is positioned lower so that small peppers may be effectively scanned. In this example both sensor arrays may be active during processing, with the software determining which array provides the most reliable readings to trigger the knife. In alternative examples the sensor arrays may be selected manually based upon the types of peppers and their sizes that are currently being processed.

The side view of the sensor arrays 3118 shows that the lane walls are V-shaped to allow closer sensor placement 3110. As the conveying belt 3108 carries the pepper 3106 past the sensor arrays 31203112, the pepper is penetrated by infrared radiation 3108. The penetrating signal produced by the transmitter array 3112 allows detection of the density of the stem, density of the placenta, and seeds which is read by the mating receiver sensors, here 3120 which read the residual signal strength.

FIG. 32 shows a pepper being de-stemmed as it enters an example of the de-stemmer machine stem first. Here are pepper is traveling stem first 3202 down a processing lane having just passed the IR RX/TX sensor array 3112. The Pepper has been scanned and a determination of the pepper's orientation (tail first or stem first), and where the shoulder is has been made based on density and or profile of the stem and placenta. After an appropriate delay time to get the pepper positioned properly, the knife is triggered. At this instant the knife 3404 has been activated and is shown just prior to de-stemming a pepper.

FIG. 33 shows a de-stemmed pepper as it leaves an example of the de-stemmer machine tail last. This figure shows the stem first pepper, with the stem removed 3304, as it exits the de-stemmer. Also shown is the calyx 3302 which has been separated from the pepper.

FIG. 34 shows a pepper being de-stemmed as it enters an example of the de-stemmer machine tail first. This figure shows a tail first pepper, with the stem removed 3402 as it exits the de-stemmer. As can be seen from the figure the machine correctly deduces whether the pepper is stem first, or tail first in the lane and appropriately de-stems the pepper.

FIG. 35 shows an example of a bounce sorting machine for separating de-stemmed peppers from the stems. Here a pepper is shown as it enters the bounce sort machine 2816. A bounce sort bar 3508 is disposed at the end of the moving conveyor belt. Due to the differing weight of the stems and the peppers pass they hit the bounce sort bar the de-stemmed peppers tend to tumble in a forward direction 3504. Stems and caps hitting the bounce sort bar 3508 tend to fall backward 3506. A conveyor belt placed to the rear can pickup the stems and a conveyor belt placed in a forward position can pick up the de-stemmed peppers.

Those skilled in the art will realize that storage devices utilized to store program instructions for pepper de-stemming can be distributed across a network, in addition to residing local to a single controller. For example, a remote computer may store an example of the process described as software. A local or terminal computer may access the remote computer and download a part or all of the software to run the program. Alternatively the local computer may download pieces of the software as needed, or distributively process by executing some software instructions at the local terminal and some at the remote computer (or computer network). Those skilled in the art will also realize that by utilizing conventional techniques known to those skilled in the art that all, or a portion of the software instructions for pepper de-stemming may be carried out by a dedicated circuit, such as a DSP, programmable logic array, or the like.

The invention claimed is:

1. A method of de-stemming peppers comprising:
loading harvested peppers into a hopper;
raising peppers to an increased height;
dropping the peppers into a vibration hopper;
distributing peppers from the vibration hopper onto a channeled vibrator to align them lengthwise; and
feeding the peppers lengthwise to a pepper de-stemming apparatus where the stems are removed by sensing the location of a pepper shoulder on a pepper to be cut, and removing the stem and calyx at the shoulder of each pepper with a double bladed knife regardless of pepper length based upon the location of the pepper shoulder as determined by a first sensor and a second sensor disposed beneath the first sensor, the first and second sensors disposed in the wall of a generally "V" shaped lane.

2. The method of de-stemming a pepper of claim 1, in which the de-stemmer examines the exterior of the pepper to determine a location on the pepper to cut off the stem.

3. The method of de-stemming a pepper of claim 1, in which the de-stemmer examines the interior of the pepper to determine a location on the pepper to cut off the stem.

4. The method of de-stemming a pepper of claim 1, in which infra red radiation is used to examine the interior of the pepper.

5. The method of de-stemming a pepper of claim 1, in which the location of the cut is located based on a strength of a received signal, indicative of the density of the pepper.

6. The method of de-stemming a pepper of claim 1, in which a cut location is determined based on the location of the placenta and a seed pod.

7. The method of de-stemming a pepper of claim 1, in which at least one sensors is used.

8. The method of de-stemming a pepper of claim 1, in which a first sensor is used to find a pepper stem, and a second sensor is used to examine a pod interior.

9. A method of de-stemming peppers comprising:

Illuminating a longitudinally oriented pepper traveling in a generally v-shaped lane, with an IR signal from a first IR transmitter disposed in a sidewall of a substantially vertical "V" shaved lane, and a second IR transmitter disposed in a sidewall below the first IR transmitter in the substantially vertical "V" shaped lane, each disposed in a first sidewall of a generally v-shaped lane;

determining a peppers orientation in a lane based upon first received information from a first sensor disposed in a second opposite sidewall of the generally v-shaped lane; and determining where to place a cut on the pepper to remove its stem based upon second received information from a second sensor disposed in the second opposite sidewall of the v-shaped lane and the first sensor.

10. The method of de-stemming a pepper of claim 8, in which de-stemming occurs after a time delay.

11. The method of de-stemming a pepper of claim 8, further comprising de-stemming the pepper by actuating a knife based on the first received information and the second received information.

12. The method of de-stemming a pepper of claim 11, in which the first sensor and the second sensor each comprise an IR emitter and an IR receiver pair.

13. The method of de-stemming a pepper of claim 12, in which the pepper passes between the IR emitter and IR receiver.

14. The method of de-stemming a pepper of claim 8, in which de-stemming is accomplished by actuating a pneumatic knife.

15. The method of de-stemming a pepper of claim 8, further comprising conveying a pepper from the first sensor, and the second sensor to the knife.

16. The method of de-stemming a pepper of claim 15, in which de-stemming the pepper is accomplished by swinging the knife in a first direction and de-stemming a second pepper is accomplished by swinging the knife in a direction opposite the first direction.

17. The method of de-stemming a pepper of claim 8, in which conveying is provided by two v-belts.

\* \* \* \* \*